US012286622B2

(12) United States Patent
Armour et al.

(10) Patent No.: US 12,286,622 B2
(45) Date of Patent: Apr. 29, 2025

(54) GENOMICS-BASED IDENTIFICATION AND CHARACTERIZATION OF RARE CELL TYPES

(71) Applicant: Auransa Inc., Palo Alto, CA (US)

(72) Inventors: Christopher Armour, Palo Alto, CA (US); Pek Yee Lum, Palo Alto, CA (US)

(73) Assignee: Auransa Inc., Palo Alto (CA)

( * ) Notice: Subject to any disclaimer, the term of this patent is extended or adjusted under 35 U.S.C. 154(b) by 975 days.

(21) Appl. No.: 17/419,422

(22) PCT Filed: Dec. 30, 2019

(86) PCT No.: PCT/US2019/068898
§ 371 (c)(1),
(2) Date: Jun. 29, 2021

(87) PCT Pub. No.: WO2020/142409
PCT Pub. Date: Jul. 9, 2020

(65) Prior Publication Data
US 2022/0056434 A1 Feb. 24, 2022

Related U.S. Application Data

(60) Provisional application No. 62/786,828, filed on Dec. 31, 2018.

(51) Int. Cl.
*C12N 15/10* (2006.01)
*C12Q 1/6876* (2018.01)
*G16B 30/10* (2019.01)

(52) U.S. Cl.
CPC ....... *C12N 15/1065* (2013.01); *C12Q 1/6876* (2013.01); *G16B 30/10* (2019.02)

(58) Field of Classification Search
CPC .......................... C12N 15/1065; C12Q 1/6879
See application file for complete search history.

(56) References Cited

U.S. PATENT DOCUMENTS

2008/0242555 A1* 10/2008 Shen .................... C12Q 1/6858
506/9

FOREIGN PATENT DOCUMENTS

| WO | 2014060483 A1 | 4/2014 |
| WO | 2014165762 A1 | 10/2014 |
| WO | 2016128758 A1 | 8/2016 |

OTHER PUBLICATIONS

Apr. 17, 2020—International Search Report and Written Opinion—Appln No. PCT/2019/068898, 13 pages.

* cited by examiner

*Primary Examiner* — Aaron A Priest
*Assistant Examiner* — Matthew Harold Raymonda
(74) *Attorney, Agent, or Firm* — Banner & Witcoff, Ltd.

(57) ABSTRACT

This disclosure provides genomics-based methods that can be used to identify, quantify, and characterize rare cell types, including circulating tumor cells.

17 Claims, 9 Drawing Sheets

Specification includes a Sequence Listing.

SEQUENCE LISTING

<160> NUMBER OF SEQ ID NOS: 278

<210> SEQ ID NO 1
<211> LENGTH: 15
<212> TYPE: DNA
<213> ORGANISM: Artificial Sequence
<220> FEATURE:
<223> OTHER INFORMATION: PM1-TAIL

<400> SEQUENCE: 1
tgccctcact gttct                                                    15

<210> SEQ ID NO 2
<211> LENGTH: 35
<212> TYPE: DNA
<213> ORGANISM: Artificial Sequence
<220> FEATURE:
<223> OTHER INFORMATION: oligodT primer
<221> NAME/KEY: misc_feature
<222> LOCATION: 35
<223> OTHER INFORMATION: a or g or c or t/u

<400> SEQUENCE: 2
tgccctcact gttcttttttt tttttttttt tttvn                             35

<210> SEQ ID NO 3
<211> LENGTH: 40
<212> TYPE: DNA
<213> ORGANISM: Homo sapiens

<400> SEQUENCE: 3
tgtgctcttc cgatctcaag agaatcccct ccatctttgg                         40

<210> SEQ ID NO 4
<211> LENGTH: 42
<212> TYPE: DNA
<213> ORGANISM: Homo sapiens

<400> SEQUENCE: 4
tgtgctcttc cgatctgaga atgtcactgt agttttgagt gt                      42

<210> SEQ ID NO 5
<211> LENGTH: 41
<212> TYPE: DNA
<213> ORGANISM: Homo sapiens

<400> SEQUENCE: 5
tgtgctcttc cgatctatta ctgatgtgac tcggttttgt c                       41

<210> SEQ ID NO 6
<211> LENGTH: 41
<212> TYPE: DNA
<213> ORGANISM: Homo sapiens

<400> SEQUENCE: 6
tgtgctcttc cgatcttgac agataggcta gtggtattgt g                       41

<210> SEQ ID NO 7
<211> LENGTH: 43
<212> TYPE: DNA
<213> ORGANISM: Homo sapiens

<400> SEQUENCE: 7
tgtgctcttc cgatctaagg ttgtaaaatg tgatgtgtat gtg                43

<210> SEQ ID NO 8
<211> LENGTH: 41
<212> TYPE: DNA
<213> ORGANISM: Homo sapiens

<400> SEQUENCE: 8
tgtgctcttc cgatcttaca acaatttgtc tgcctccaag g                  41

<210> SEQ ID NO 9
<211> LENGTH: 44
<212> TYPE: DNA
<213> ORGANISM: Homo sapiens

<400> SEQUENCE: 9
tgtgctcttc cgatctaaag cagttgaaca aaaattatgg catt               44

<210> SEQ ID NO 10
<211> LENGTH: 42
<212> TYPE: DNA
<213> ORGANISM: Homo sapiens

<400> SEQUENCE: 10
tgtgctcttc cgatcttgtt ttaaaatgtt tggcagttcc ac                 42

<210> SEQ ID NO 11
<211> LENGTH: 41
<212> TYPE: DNA
<213> ORGANISM: Homo sapiens

<400> SEQUENCE: 11
tgtgctcttc cgatctggta ttttccccct tttctgcatt t                  41

<210> SEQ ID NO 12
<211> LENGTH: 40
<212> TYPE: DNA
<213> ORGANISM: Homo sapiens

<400> SEQUENCE: 12
tgtgctcttc cgatcttgat tgagcctcag aatcatttgg                    40

<210> SEQ ID NO 13
<211> LENGTH: 41
<212> TYPE: DNA
<213> ORGANISM: Homo sapiens

<400> SEQUENCE: 13
tgtgctcttc cgatctcagt ctactcagct tgacaagtgt t                  41

<210> SEQ ID NO 14
<211> LENGTH: 39
<212> TYPE: DNA
<213> ORGANISM: Homo sapiens

<400> SEQUENCE: 14
tgtgctcttc cgatctgatt ggagtaggct acagtgagg                     39

<210> SEQ ID NO 15
<211> LENGTH: 38
<212> TYPE: DNA
<213> ORGANISM: Homo sapiens -continued

```
<400> SEQUENCE: 15
tgtgctcttc cgatctcagc acggtgatta gtcccaga                                38

<210> SEQ ID NO 16
<211> LENGTH: 38
<212> TYPE: DNA
<213> ORGANISM: Homo sapiens

<400> SEQUENCE: 16
tgtgctcttc cgatctggat tcatggggag cctcacag                                38

<210> SEQ ID NO 17
<211> LENGTH: 41
<212> TYPE: DNA
<213> ORGANISM: Homo sapiens

<400> SEQUENCE: 17
tgtgctcttc cgatctttat tttgaatgat gagccttcgt g                            41

<210> SEQ ID NO 18
<211> LENGTH: 37
<212> TYPE: DNA
<213> ORGANISM: Homo sapiens

<400> SEQUENCE: 18
tgtgctcttc cgatctagac cctcactgct ggggagt                                 37

<210> SEQ ID NO 19
<211> LENGTH: 42
<212> TYPE: DNA
<213> ORGANISM: Homo sapiens

<400> SEQUENCE: 19
tgtgctcttc cgatcttgca tttattaaca tttgcaggac ac                           42

<210> SEQ ID NO 20
<211> LENGTH: 40
<212> TYPE: DNA
<213> ORGANISM: Homo sapiens

<400> SEQUENCE: 20
tgtgctcttc cgatctgtct ccagacagct ccatcaggaa                              40

<210> SEQ ID NO 21
<211> LENGTH: 41
<212> TYPE: DNA
<213> ORGANISM: Homo sapiens

<400> SEQUENCE: 21
tgtgctcttc cgatctagaa gctgcaaaat ccgatgagac t                            41

<210> SEQ ID NO 22
<211> LENGTH: 41
<212> TYPE: DNA
<213> ORGANISM: Homo sapiens

<400> SEQUENCE: 22
tgtgctcttc cgatctgaaa acctccttta ccagatgctg a                            41

<210> SEQ ID NO 23
<211> LENGTH: 41
<212> TYPE: DNA
<213> ORGANISM: Homo sapiens
```

```
<400> SEQUENCE: 23
tgtgctcttc cgatctaatg gcaacaggaa ttttcattgg t                  41

<210> SEQ ID NO 24
<211> LENGTH: 36
<212> TYPE: DNA
<213> ORGANISM: Homo sapiens

<400> SEQUENCE: 24
tgtgctcttc cgatctcatg tctgcacctc cgcttg                       36

<210> SEQ ID NO 25
<211> LENGTH: 42
<212> TYPE: DNA
<213> ORGANISM: Homo sapiens

<400> SEQUENCE: 25
tgtgctcttc cgatctcatt aaaagttggc ctgaaagtca ga                42

<210> SEQ ID NO 26
<211> LENGTH: 41
<212> TYPE: DNA
<213> ORGANISM: Homo sapiens

<400> SEQUENCE: 26
tgtgctcttc cgatctccag aacttggact ccatcgttaa a                 41

<210> SEQ ID NO 27
<211> LENGTH: 41
<212> TYPE: DNA
<213> ORGANISM: Homo sapiens

<400> SEQUENCE: 27
tgtgctcttc cgatctattt tgcaaacaat ttggagccat t                 41

<210> SEQ ID NO 28
<211> LENGTH: 43
<212> TYPE: DNA
<213> ORGANISM: Homo sapiens

<400> SEQUENCE: 28
tgtgctcttc cgatctttct taacaaccga cactcctaca aga               43

<210> SEQ ID NO 29
<211> LENGTH: 41
<212> TYPE: DNA
<213> ORGANISM: Homo sapiens

<400> SEQUENCE: 29
tgtgctcttc cgatctaaag cttaccagtg tggacttggt g                 41

<210> SEQ ID NO 30
<211> LENGTH: 46
<212> TYPE: DNA
<213> ORGANISM: Homo sapiens

<400> SEQUENCE: 30
tgtgctcttc cgatctacac acataacaag tctatgatca ttttgc            46

<210> SEQ ID NO 31
<211> LENGTH: 39
<212> TYPE: DNA
```

<213> ORGANISM: Homo sapiens

<400> SEQUENCE: 31
tgtgctcttc cgatctggcc cacaagtatc actaagctc          39

<210> SEQ ID NO 32
<211> LENGTH: 35
<212> TYPE: DNA
<213> ORGANISM: Artificial Sequence
<220> FEATURE:
<223> OTHER INFORMATION: TP53 EXON 10 gDNA forward primer

<400> SEQUENCE: 32
tgccctcact gttctcacag caggccagtg tgcag              35

<210> SEQ ID NO 33
<211> LENGTH: 38
<212> TYPE: DNA
<213> ORGANISM: Artificial Sequence
<220> FEATURE:
<223> OTHER INFORMATION: TP53 EXON 10 gDNA reverse primer

<400> SEQUENCE: 33
tgtgctcttc cgatctttgg gcctgtgtta tctcctag           38

<210> SEQ ID NO 34
<211> LENGTH: 38
<212> TYPE: DNA
<213> ORGANISM: Artificial Sequence
<220> FEATURE:
<223> OTHER INFORMATION: TP53 EXON 2 gDNA forward primer

<400> SEQUENCE: 34
tgccctcact gttctgaaaa gagcagtcag aggaccag           38

<210> SEQ ID NO 35
<211> LENGTH: 41
<212> TYPE: DNA
<213> ORGANISM: Artificial Sequence
<220> FEATURE:
<223> OTHER INFORMATION: TP53 EXON 2 gDNA reverse primer

<400> SEQUENCE: 35
tgtgctcttc cgatctaatt ccatgggact gactttctgc t        41

<210> SEQ ID NO 36
<211> LENGTH: 36
<212> TYPE: DNA
<213> ORGANISM: Artificial Sequence
<220> FEATURE:
<223> OTHER INFORMATION: TP53 EXON 4 gDNA forward primer

<400> SEQUENCE: 36
tgccctcact gttctaacca gccctgtcgt ctctcc             36

<210> SEQ ID NO 37
<211> LENGTH: 41
<212> TYPE: DNA
<213> ORGANISM: Artificial Sequence
<220> FEATURE:
<223> OTHER INFORMATION: TP53 EXON 4 gDNA reverse primer

<400> SEQUENCE: 37
tgtgctcttc cgatctcttg tgccctgact ttcaactctg t        41

```
<210> SEQ ID NO 38
<211> LENGTH: 37
<212> TYPE: DNA
<213> ORGANISM: Artificial Sequence
<220> FEATURE:
<223> OTHER INFORMATION: TP53 EXON 5 gDNA forward primer

<400> SEQUENCE: 38
tgccctcact gttctcttaa cccctcctcc cagagac                            37

<210> SEQ ID NO 39
<211> LENGTH: 40
<212> TYPE: DNA
<213> ORGANISM: Artificial Sequence
<220> FEATURE:
<223> OTHER INFORMATION: TP53 EXON 5 gDNA reverse primer

<400> SEQUENCE: 39
tgtgctcttc cgatctctct gattcctcac tgattgctct                         40

<210> SEQ ID NO 40
<211> LENGTH: 38
<212> TYPE: DNA
<213> ORGANISM: Artificial Sequence
<220> FEATURE:
<223> OTHER INFORMATION: TP53 EXON 6 gDNA forward primer

<400> SEQUENCE: 40
tgccctcact gttcttgggg aacaagaagt ggagaatg                           38

<210> SEQ ID NO 41
<211> LENGTH: 39
<212> TYPE: DNA
<213> ORGANISM: Artificial Sequence
<220> FEATURE:
<223> OTHER INFORMATION: TP53 EXON 6 gDNA reverse primer

<400> SEQUENCE: 41
tgtgctcttc cgatctcaga ccctctcact catgtgatg                          39

<210> SEQ ID NO 42
<211> LENGTH: 36
<212> TYPE: DNA
<213> ORGANISM: Artificial Sequence
<220> FEATURE:
<223> OTHER INFORMATION: TP53 EXON 7 gDNA forward primer

<400> SEQUENCE: 42
tgccctcact gttctcagga aggggctgag gtcact                             36

<210> SEQ ID NO 43
<211> LENGTH: 39
<212> TYPE: DNA
<213> ORGANISM: Artificial Sequence
<220> FEATURE:
<223> OTHER INFORMATION: TP53 EXON 7 gDNA reverse primer

<400> SEQUENCE: 43
tgtgctcttc cgatctactt ctccccctcc tctgttgct                          39

<210> SEQ ID NO 44
<211> LENGTH: 38
<212> TYPE: DNA
<213> ORGANISM: Artificial Sequence
<220> FEATURE:
<223> OTHER INFORMATION: TP53 EXON 8 gDNA forward primer
```

<400> SEQUENCE: 44
tgccctcact gttctcactt gataagaggt cccaagac    38

<210> SEQ ID NO 45
<211> LENGTH: 39
<212> TYPE: DNA
<213> ORGANISM: Artificial Sequence
<220> FEATURE:
<223> OTHER INFORMATION: TP53 EXON 8 gDNA reverse primer

<400> SEQUENCE: 45
tgtgctcttc cgatctgtgc agttatgcct cagattcac    39

<210> SEQ ID NO 46
<211> LENGTH: 37
<212> TYPE: DNA
<213> ORGANISM: Artificial Sequence
<220> FEATURE:
<223> OTHER INFORMATION: TP53 EXON 9 gDNA forward primer

<400> SEQUENCE: 46
tgccctcact gttctgtctc ctccaccgct tcttgtc    37

<210> SEQ ID NO 47
<211> LENGTH: 41
<212> TYPE: DNA
<213> ORGANISM: Artificial Sequence
<220> FEATURE:
<223> OTHER INFORMATION: TP53 EXON 9 gDNA reverse primer

<400> SEQUENCE: 47
tgtgctcttc cgatcttcct tactgcctct tgcttctctt t    41

<210> SEQ ID NO 48
<211> LENGTH: 42
<212> TYPE: DNA
<213> ORGANISM: Artificial Sequence
<220> FEATURE:
<223> OTHER INFORMATION: PIK3CA E545K gDNA forward primer

<400> SEQUENCE: 48
tgccctcact gttctttgct ttttctgtaa atcatctgtg aa    42

<210> SEQ ID NO 49
<211> LENGTH: 41
<212> TYPE: DNA
<213> ORGANISM: Artificial Sequence
<220> FEATURE:
<223> OTHER INFORMATION: PIK3CA E545K gDNA reverse primer

<400> SEQUENCE: 49
tgtgctcttc cgatctatgc tgagatcagc caaattcagt t    41

<210> SEQ ID NO 50
<211> LENGTH: 41
<212> TYPE: DNA
<213> ORGANISM: Artificial Sequence
<220> FEATURE:
<223> OTHER INFORMATION: EP300_4066 gDNA forward primer

<400> SEQUENCE: 50
tgccctcact gttctttggt gattccagtc tgaatgagtt a    41

<210> SEQ ID NO 51
<211> LENGTH: 41

```
<212> TYPE: DNA
<213> ORGANISM: Artificial Sequence
<220> FEATURE:
<223> OTHER INFORMATION: EP300_4066 gDNA reverse primer

<400> SEQUENCE: 51
tgtgctcttc cgatctaagc acaggtcaac accatcaatt t           41

<210> SEQ ID NO 52
<211> LENGTH: 36
<212> TYPE: DNA
<213> ORGANISM: Artificial Sequence
<220> FEATURE:
<223> OTHER INFORMATION: PTPRD_2388 gDNA forward primer

<400> SEQUENCE: 52
tgccctcact gttctgtgga caccagtttg ggcttg                 36

<210> SEQ ID NO 53
<211> LENGTH: 41
<212> TYPE: DNA
<213> ORGANISM: Artificial Sequence
<220> FEATURE:
<223> OTHER INFORMATION: PTPRD_2388 gDNA reverse primer

<400> SEQUENCE: 53
tgtgctcttc cgatctttt cccccagagc attagtagca t            41

<210> SEQ ID NO 54
<211> LENGTH: 38
<212> TYPE: DNA
<213> ORGANISM: Artificial Sequence
<220> FEATURE:
<223> OTHER INFORMATION: PEX14_794 gDNA forward primer

<400> SEQUENCE: 54
tgccctcact gttctctggc agatcccagt caagtcac               38

<210> SEQ ID NO 55
<211> LENGTH: 40
<212> TYPE: DNA
<213> ORGANISM: Artificial Sequence
<220> FEATURE:
<223> OTHER INFORMATION: PEX14_794 gDNA reverse primer

<400> SEQUENCE: 55
tgtgctcttc cgatctagca agtggtaggt gaccgtggag             40

<210> SEQ ID NO 56
<211> LENGTH: 33
<212> TYPE: DNA
<213> ORGANISM: Artificial Sequence
<220> FEATURE:
<223> OTHER INFORMATION: PM1-SEQ

<400> SEQUENCE: 56
acaccgcaag tccactaatg ccctcactgt tct                    33

<210> SEQ ID NO 57
<211> LENGTH: 34
<212> TYPE: DNA
<213> ORGANISM: Artificial Sequence
<220> FEATURE:
<223> OTHER INFORMATION: P7 sequence

<400> SEQUENCE: 57
```
gtgactggag ttcagacgtg tgctcttccg atct                              34

<210> SEQ ID NO 58
<211> LENGTH: 58
<212> TYPE: DNA
<213> ORGANISM: Artificial Sequence
<220> FEATURE:
<223> OTHER INFORMATION: P5PM1

<400> SEQUENCE: 58
aatgatacgg cgaccaccga gatcaacacc gcaagtccac taatgccctc actgttct    58

<210> SEQ ID NO 59
<211> LENGTH: 69
<212> TYPE: DNA
<213> ORGANISM: Artificial Sequence
<220> FEATURE:
<223> OTHER INFORMATION: P7 INDEX#001

<400> SEQUENCE: 59
caagcagaag acggcatacg agatatctag ccggccgtga ctggagttca gacgtgtgct    60
cttccgatc                                                           69

<210> SEQ ID NO 60
<211> LENGTH: 69
<212> TYPE: DNA
<213> ORGANISM: Artificial Sequence
<220> FEATURE:
<223> OTHER INFORMATION: P7 INDEX#002

<400> SEQUENCE: 60
caagcagaag acggcatacg agataaggaa gagatagtga ctggagttca gacgtgtgct    60
cttccgatc                                                           69

<210> SEQ ID NO 61
<211> LENGTH: 69
<212> TYPE: DNA
<213> ORGANISM: Artificial Sequence
<220> FEATURE:
<223> OTHER INFORMATION: P7 INDEX#003

<400> SEQUENCE: 61
caagcagaag acggcatacg agatggacgg catctagtga ctggagttca gacgtgtgct    60
cttccgatc                                                           69

<210> SEQ ID NO 62
<211> LENGTH: 69
<212> TYPE: DNA
<213> ORGANISM: Artificial Sequence
<220> FEATURE:
<223> OTHER INFORMATION: P7 INDEX#004

<400> SEQUENCE: 62
caagcagaag acggcatacg agataaggaa ggagcggtga ctggagttca gacgtgtgct    60
cttccgatc                                                           69

<210> SEQ ID NO 63
<211> LENGTH: 69
<212> TYPE: DNA
<213> ORGANISM: Artificial Sequence
<220> FEATURE:
<223> OTHER INFORMATION: P7 INDEX#005

<400> SEQUENCE: 63
caagcagaag acggcatacg agatggacgg cgctcggtga ctggagttca gacgtgtgct    60
cttccgatc                                                            69

<210> SEQ ID NO 64
<211> LENGTH: 69
<212> TYPE: DNA
<213> ORGANISM: Artificial Sequence
<220> FEATURE:
<223> OTHER INFORMATION: P7 INDEX#006

<400> SEQUENCE: 64
caagcagaag acggcatacg agatccggac tctcgagtga ctggagttca gacgtgtgct    60
cttccgatc                                                            69

<210> SEQ ID NO 65
<211> LENGTH: 69
<212> TYPE: DNA
<213> ORGANISM: Artificial Sequence
<220> FEATURE:
<223> OTHER INFORMATION: P7 INDEX#007

<400> SEQUENCE: 65
caagcagaag acggcatacg agatggccgg ccgagcgtga ctggagttca gacgtgtgct    60
cttccgatc                                                            69

<210> SEQ ID NO 66
<211> LENGTH: 69
<212> TYPE: DNA
<213> ORGANISM: Artificial Sequence
<220> FEATURE:
<223> OTHER INFORMATION: P7 INDEX#008

<400> SEQUENCE: 66
caagcagaag acggcatacg agatccggac tgagctgtga ctggagttca gacgtgtgct    60
cttccgatc                                                            69

<210> SEQ ID NO 67
<211> LENGTH: 69
<212> TYPE: DNA
<213> ORGANISM: Artificial Sequence
<220> FEATURE:
<223> OTHER INFORMATION: P7 INDEX#009

<400> SEQUENCE: 67
caagcagaag acggcatacg agatggacgc ggcagtgtga ctggagttca gacgtgtgct    60
cttccgatc                                                            69

<210> SEQ ID NO 68
<211> LENGTH: 69
<212> TYPE: DNA
<213> ORGANISM: Artificial Sequence
<220> FEATURE:
<223> OTHER INFORMATION: P7 INDEX#010

<400> SEQUENCE: 68
caagcagaag acggcatacg agatccggag aagtaagtga ctggagttca gacgtgtgct    60
cttccgatc                                                            69

<210> SEQ ID NO 69
<211> LENGTH: 69
<212> TYPE: DNA

```
<213> ORGANISM: Artificial Sequence
<220> FEATURE:
<223> OTHER INFORMATION: P7 INDEX#011

<400> SEQUENCE: 69
caagcagaag acggcatacg agatggccgc gcgtcagtga ctggagttca gacgtgtgct      60
cttccgatc                                                              69

<210> SEQ ID NO 70
<211> LENGTH: 69
<212> TYPE: DNA
<213> ORGANISM: Artificial Sequence
<220> FEATURE:
<223> OTHER INFORMATION: P7 INDEX#012

<400> SEQUENCE: 70
caagcagaag acggcatacg agatccggag atcattgtga ctggagttca gacgtgtgct      60
cttccgatc                                                              69

<210> SEQ ID NO 71
<211> LENGTH: 69
<212> TYPE: DNA
<213> ORGANISM: Artificial Sequence
<220> FEATURE:
<223> OTHER INFORMATION: P7 INDEX#013

<400> SEQUENCE: 71
caagcagaag acggcatacg agatggacgt acgcttgtga ctggagttca gacgtgtgct      60
cttccgatc                                                              69

<210> SEQ ID NO 72
<211> LENGTH: 69
<212> TYPE: DNA
<213> ORGANISM: Artificial Sequence
<220> FEATURE:
<223> OTHER INFORMATION: P7 INDEX#014

<400> SEQUENCE: 72
caagcagaag acggcatacg agataaggac tgataagtga ctggagttca gacgtgtgct      60
cttccgatc                                                              69

<210> SEQ ID NO 73
<211> LENGTH: 69
<212> TYPE: DNA
<213> ORGANISM: Artificial Sequence
<220> FEATURE:
<223> OTHER INFORMATION: P7 INDEX#015

<400> SEQUENCE: 73
caagcagaag acggcatacg agatggacgc gatgacgtga ctggagttca gacgtgtgct      60
cttccgatc                                                              69

<210> SEQ ID NO 74
<211> LENGTH: 69
<212> TYPE: DNA
<213> ORGANISM: Artificial Sequence
<220> FEATURE:
<223> OTHER INFORMATION: P7 INDEX#016

<400> SEQUENCE: 74
caagcagaag acggcatacg agatccggag agacgggtga ctggagttca gacgtgtgct      60
cttccgatc                                                              69
```

<210> SEQ ID NO 75
<211> LENGTH: 69
<212> TYPE: DNA
<213> ORGANISM: Artificial Sequence
<220> FEATURE:
<223> OTHER INFORMATION: P7 INDEX#017

<400> SEQUENCE: 75
caagcagaag acggcatacg agatggacgt agcgaagtga ctggagttca gacgtgtgct     60
cttccgatc                                                            69

<210> SEQ ID NO 76
<211> LENGTH: 69
<212> TYPE: DNA
<213> ORGANISM: Artificial Sequence
<220> FEATURE:
<223> OTHER INFORMATION: P7 INDEX#018

<400> SEQUENCE: 76
caagcagaag acggcatacg agatccggaa gagcgtgtga ctggagttca gacgtgtgct     60
cttccgatc                                                            69

<210> SEQ ID NO 77
<211> LENGTH: 69
<212> TYPE: DNA
<213> ORGANISM: Artificial Sequence
<220> FEATURE:
<223> OTHER INFORMATION: P7 INDEX#019

<400> SEQUENCE: 77
caagcagaag acggcatacg agatggccgc gtactggtga ctggagttca gacgtgtgct     60
cttccgatc                                                            69

<210> SEQ ID NO 78
<211> LENGTH: 69
<212> TYPE: DNA
<213> ORGANISM: Artificial Sequence
<220> FEATURE:
<223> OTHER INFORMATION: P7 INDEX#020

<400> SEQUENCE: 78
caagcagaag acggcatacg agataaggat cagtacgtga ctggagttca gacgtgtgct     60
cttccgatc                                                            69

<210> SEQ ID NO 79
<211> LENGTH: 69
<212> TYPE: DNA
<213> ORGANISM: Artificial Sequence
<220> FEATURE:
<223> OTHER INFORMATION: P7 INDEX#021

<400> SEQUENCE: 79
caagcagaag acggcatacg agatggccgt atatccgtga ctggagttca gacgtgtgct     60
cttccgatc                                                            69

<210> SEQ ID NO 80
<211> LENGTH: 69
<212> TYPE: DNA
<213> ORGANISM: Artificial Sequence
<220> FEATURE:
<223> OTHER INFORMATION: P7 INDEX#022

-continued

```
<400> SEQUENCE: 80
caagcagaag acggcatacg agatccggaa gctatggtga ctggagttca gacgtgtgct    60
cttccgatc                                                            69

<210> SEQ ID NO 81
<211> LENGTH: 69
<212> TYPE: DNA
<213> ORGANISM: Artificial Sequence
<220> FEATURE:
<223> OTHER INFORMATION: P7 INDEX#023

<400> SEQUENCE: 81
caagcagaag acggcatacg agatggccga tgcctcgtga ctggagttca gacgtgtgct    60
cttccgatc                                                            69

<210> SEQ ID NO 82
<211> LENGTH: 69
<212> TYPE: DNA
<213> ORGANISM: Artificial Sequence
<220> FEATURE:
<223> OTHER INFORMATION: P7 INDEX#024

<400> SEQUENCE: 82
caagcagaag acggcatacg agatccggat ccttatgtga ctggagttca gacgtgtgct    60
cttccgatc                                                            69

<210> SEQ ID NO 83
<211> LENGTH: 69
<212> TYPE: DNA
<213> ORGANISM: Artificial Sequence
<220> FEATURE:
<223> OTHER INFORMATION: P7 INDEX#025

<400> SEQUENCE: 83
caagcagaag acggcatacg agatggacga tcggaggtga ctggagttca gacgtgtgct    60
cttccgatc                                                            69

<210> SEQ ID NO 84
<211> LENGTH: 69
<212> TYPE: DNA
<213> ORGANISM: Artificial Sequence
<220> FEATURE:
<223> OTHER INFORMATION: P7 INDEX#026

<400> SEQUENCE: 84
caagcagaag acggcatacg agatccggat cgaatagtga ctggagttca gacgtgtgct    60
cttccgatc                                                            69

<210> SEQ ID NO 85
<211> LENGTH: 69
<212> TYPE: DNA
<213> ORGANISM: Artificial Sequence
<220> FEATURE:
<223> OTHER INFORMATION: P7 INDEX#027

<400> SEQUENCE: 85
caagcagaag acggcatacg agatggacga ttaagagtga ctggagttca gacgtgtgct    60
cttccgatc                                                            69

<210> SEQ ID NO 86
<211> LENGTH: 69
```

```
<212> TYPE: DNA
<213> ORGANISM: Artificial Sequence
<220> FEATURE:
<223> OTHER INFORMATION: P7 INDEX#028

<400> SEQUENCE: 86
caagcagaag acggcatacg agatccggat caggcggtga ctggagttca gacgtgtgct      60
cttccgatc                                                              69

<210> SEQ ID NO 87
<211> LENGTH: 69
<212> TYPE: DNA
<213> ORGANISM: Artificial Sequence
<220> FEATURE:
<223> OTHER INFORMATION: P7 INDEX#029

<400> SEQUENCE: 87
caagcagaag acggcatacg agatggacga tattctgtga ctggagttca gacgtgtgct      60
cttccgatc                                                              69

<210> SEQ ID NO 88
<211> LENGTH: 69
<212> TYPE: DNA
<213> ORGANISM: Artificial Sequence
<220> FEATURE:
<223> OTHER INFORMATION: P7 INDEX#030

<400> SEQUENCE: 88
caagcagaag acggcatacg agatccggat ctccgcgtga ctggagttca gacgtgtgct      60
cttccgatc                                                              69

<210> SEQ ID NO 89
<211> LENGTH: 69
<212> TYPE: DNA
<213> ORGANISM: Artificial Sequence
<220> FEATURE:
<223> OTHER INFORMATION: P7 INDEX#031

<400> SEQUENCE: 89
caagcagaag acggcatacg agatggaccg gccatggtga ctggagttca gacgtgtgct      60
cttccgatc                                                              69

<210> SEQ ID NO 90
<211> LENGTH: 69
<212> TYPE: DNA
<213> ORGANISM: Artificial Sequence
<220> FEATURE:
<223> OTHER INFORMATION: P7 INDEX#032

<400> SEQUENCE: 90
caagcagaag acggcatacg agataaggta cgtgacgtga ctggagttca gacgtgtgct      60
cttccgatc                                                              69

<210> SEQ ID NO 91
<211> LENGTH: 69
<212> TYPE: DNA
<213> ORGANISM: Artificial Sequence
<220> FEATURE:
<223> OTHER INFORMATION: P7 INDEX#033

<400> SEQUENCE: 91
caagcagaag acggcatacg agatggaccg gttgcagtga ctggagttca gacgtgtgct      60
``` cttccgatc 69

<210> SEQ ID NO 92
<211> LENGTH: 69
<212> TYPE: DNA
<213> ORGANISM: Artificial Sequence
<220> FEATURE:
<223> OTHER INFORMATION: P7 INDEX#034

<400> SEQUENCE: 92
caagcagaag acggcatacg agatccggtc aacagggtga ctggagttca gacgtgtgct 60
cttccgatc 69

<210> SEQ ID NO 93
<211> LENGTH: 69
<212> TYPE: DNA
<213> ORGANISM: Artificial Sequence
<220> FEATURE:
<223> OTHER INFORMATION: P7 INDEX#035

<400> SEQUENCE: 93
caagcagaag acggcatacg agatggacct tgggctgtga ctggagttca gacgtgtgct 60
cttccgatc 69

<210> SEQ ID NO 94
<211> LENGTH: 69
<212> TYPE: DNA
<213> ORGANISM: Artificial Sequence
<220> FEATURE:
<223> OTHER INFORMATION: P7 INDEX#036

<400> SEQUENCE: 94
caagcagaag acggcatacg agatccggta ccaagcgtga ctggagttca gacgtgtgct 60
cttccgatc 69

<210> SEQ ID NO 95
<211> LENGTH: 69
<212> TYPE: DNA
<213> ORGANISM: Artificial Sequence
<220> FEATURE:
<223> OTHER INFORMATION: P7 INDEX#037

<400> SEQUENCE: 95
caagcagaag acggcatacg agatggacct tcccgagtga ctggagttca gacgtgtgct 60
cttccgatc 69

<210> SEQ ID NO 96
<211> LENGTH: 69
<212> TYPE: DNA
<213> ORGANISM: Artificial Sequence
<220> FEATURE:
<223> OTHER INFORMATION: P7 INDEX#038

<400> SEQUENCE: 96
caagcagaag acggcatacg agatccggta cgttcggtga ctggagttca gacgtgtgct 60
cttccgatc 69

<210> SEQ ID NO 97
<211> LENGTH: 69
<212> TYPE: DNA
<213> ORGANISM: Artificial Sequence
<220> FEATURE:
<223> OTHER INFORMATION: P7 INDEX#039

<400> SEQUENCE: 97
caagcagaag acggcatacg agatggccct taaatcgtga ctggagttca gacgtgtgct        60
cttccgatc                                                                69

<210> SEQ ID NO 98
<211> LENGTH: 69
<212> TYPE: DNA
<213> ORGANISM: Artificial Sequence
<220> FEATURE:
<223> OTHER INFORMATION: P7 INDEX#040

<400> SEQUENCE: 98
caagcagaag acggcatacg agataaggtc agttctgtga ctggagttca gacgtgtgct        60
cttccgatc                                                                69

<210> SEQ ID NO 99
<211> LENGTH: 69
<212> TYPE: DNA
<213> ORGANISM: Artificial Sequence
<220> FEATURE:
<223> OTHER INFORMATION: P7 INDEX#041

<400> SEQUENCE: 99
caagcagaag acggcatacg agatggacca aggcgggtga ctggagttca gacgtgtgct        60
cttccgatc                                                                69

<210> SEQ ID NO 100
<211> LENGTH: 69
<212> TYPE: DNA
<213> ORGANISM: Artificial Sequence
<220> FEATURE:
<223> OTHER INFORMATION: P7 INDEX#042

<400> SEQUENCE: 100
caagcagaag acggcatacg agatccggtt gcatcagtga ctggagttca gacgtgtgct        60
cttccgatc                                                                69

<210> SEQ ID NO 101
<211> LENGTH: 69
<212> TYPE: DNA
<213> ORGANISM: Artificial Sequence
<220> FEATURE:
<223> OTHER INFORMATION: P7 INDEX#043

<400> SEQUENCE: 101
caagcagaag acggcatacg agatggccca accgccgtga ctggagttca gacgtgtgct        60
cttccgatc                                                                69

<210> SEQ ID NO 102
<211> LENGTH: 69
<212> TYPE: DNA
<213> ORGANISM: Artificial Sequence
<220> FEATURE:
<223> OTHER INFORMATION: P7 INDEX#044

<400> SEQUENCE: 102
caagcagaag acggcatacg agatccggtt ggtagtgtga ctggagttca gacgtgtgct        60
cttccgatc                                                                69

<210> SEQ ID NO 103

```
<211> LENGTH: 69
<212> TYPE: DNA
<213> ORGANISM: Artificial Sequence
<220> FEATURE:
<223> OTHER INFORMATION: P7 INDEX#045

<400> SEQUENCE: 103
caagcagaag acggcatacg agatggacca attattgtga ctggagttca gacgtgtgct      60
cttccgatc                                                             69

<210> SEQ ID NO 104
<211> LENGTH: 69
<212> TYPE: DNA
<213> ORGANISM: Artificial Sequence
<220> FEATURE:
<223> OTHER INFORMATION: P7 INDEX#046

<400> SEQUENCE: 104
caagcagaag acggcatacg agatccggtt gacgacgtga ctggagttca gacgtgtgct      60
cttccgatc                                                             69

<210> SEQ ID NO 105
<211> LENGTH: 69
<212> TYPE: DNA
<213> ORGANISM: Artificial Sequence
<220> FEATURE:
<223> OTHER INFORMATION: P7 INDEX#047

<400> SEQUENCE: 105
caagcagaag acggcatacg agatggcctg agatttgtga ctggagttca gacgtgtgct      60
cttccgatc                                                             69

<210> SEQ ID NO 106
<211> LENGTH: 69
<212> TYPE: DNA
<213> ORGANISM: Artificial Sequence
<220> FEATURE:
<223> OTHER INFORMATION: P7 INDEX#048

<400> SEQUENCE: 106
caagcagaag acggcatacg agatccggcc gcgcacgtga ctggagttca gacgtgtgct      60
cttccgatc                                                             69

<210> SEQ ID NO 107
<211> LENGTH: 69
<212> TYPE: DNA
<213> ORGANISM: Artificial Sequence
<220> FEATURE:
<223> OTHER INFORMATION: P7 INDEX#049

<400> SEQUENCE: 107
caagcagaag acggcatacg agatggactg actaaagtga ctggagttca gacgtgtgct      60
cttccgatc                                                             69

<210> SEQ ID NO 108
<211> LENGTH: 69
<212> TYPE: DNA
<213> ORGANISM: Artificial Sequence
<220> FEATURE:
<223> OTHER INFORMATION: P7 INDEX#050

<400> SEQUENCE: 108
caagcagaag acggcatacg agatccggcc ggcgtggtga ctggagttca gacgtgtgct      60
``` cttccgatc                                                              69

<210> SEQ ID NO 109
<211> LENGTH: 69
<212> TYPE: DNA
<213> ORGANISM: Artificial Sequence
<220> FEATURE:
<223> OTHER INFORMATION: P7 INDEX#051

<400> SEQUENCE: 109
caagcagaag acggcatacg agatggactg atcggggtga ctggagttca gacgtgtgct    60
cttccgatc                                                              69

<210> SEQ ID NO 110
<211> LENGTH: 69
<212> TYPE: DNA
<213> ORGANISM: Artificial Sequence
<220> FEATURE:
<223> OTHER INFORMATION: P7 INDEX#052

<400> SEQUENCE: 110
caagcagaag acggcatacg agatccggcc gatacagtga ctggagttca gacgtgtgct    60
cttccgatc                                                              69

<210> SEQ ID NO 111
<211> LENGTH: 69
<212> TYPE: DNA
<213> ORGANISM: Artificial Sequence
<220> FEATURE:
<223> OTHER INFORMATION: P7 INDEX#053

<400> SEQUENCE: 111
caagcagaag acggcatacg agatggactc tgaaaggtga ctggagttca gacgtgtgct    60
cttccgatc                                                              69

<210> SEQ ID NO 112
<211> LENGTH: 69
<212> TYPE: DNA
<213> ORGANISM: Artificial Sequence
<220> FEATURE:
<223> OTHER INFORMATION: P7 INDEX#054

<400> SEQUENCE: 112
caagcagaag acggcatacg agatccggcg ccggtagtga ctggagttca gacgtgtgct    60
cttccgatc                                                              69

<210> SEQ ID NO 113
<211> LENGTH: 69
<212> TYPE: DNA
<213> ORGANISM: Artificial Sequence
<220> FEATURE:
<223> OTHER INFORMATION: P7 INDEX#055

<400> SEQUENCE: 113
caagcagaag acggcatacg agatggactc tctttcgtga ctggagttca gacgtgtgct    60
cttccgatc                                                              69

<210> SEQ ID NO 114
<211> LENGTH: 69
<212> TYPE: DNA
<213> ORGANISM: Artificial Sequence
<220> FEATURE:

<223> OTHER INFORMATION: P7 INDEX#056

<400> SEQUENCE: 114
caagcagaag acggcatacg agataaggct agccaggtga ctggagttca gacgtgtgct      60
cttccgatc                                                            69

<210> SEQ ID NO 115
<211> LENGTH: 69
<212> TYPE: DNA
<213> ORGANISM: Artificial Sequence
<220> FEATURE:
<223> OTHER INFORMATION: P7 INDEX#057

<400> SEQUENCE: 115
caagcagaag acggcatacg agatggcctc ttccctgtga ctggagttca gacgtgtgct      60
cttccgatc                                                            69

<210> SEQ ID NO 116
<211> LENGTH: 69
<212> TYPE: DNA
<213> ORGANISM: Artificial Sequence
<220> FEATURE:
<223> OTHER INFORMATION: P7 INDEX#058

<400> SEQUENCE: 116
caagcagaag acggcatacg agataaggct acggtcgtga ctggagttca gacgtgtgct      60
cttccgatc                                                            69

<210> SEQ ID NO 117
<211> LENGTH: 69
<212> TYPE: DNA
<213> ORGANISM: Artificial Sequence
<220> FEATURE:
<223> OTHER INFORMATION: P7 INDEX#059

<400> SEQUENCE: 117
caagcagaag acggcatacg agatggactc tagggagtga ctggagttca gacgtgtgct      60
cttccgatc                                                            69

<210> SEQ ID NO 118
<211> LENGTH: 69
<212> TYPE: DNA
<213> ORGANISM: Artificial Sequence
<220> FEATURE:
<223> OTHER INFORMATION: P7 INDEX#060

<400> SEQUENCE: 118
caagcagaag acggcatacg agataaggct ataactgtga ctggagttca gacgtgtgct      60
cttccgatc                                                            69

<210> SEQ ID NO 119
<211> LENGTH: 69
<212> TYPE: DNA
<213> ORGANISM: Artificial Sequence
<220> FEATURE:
<223> OTHER INFORMATION: P7 INDEX#061

<400> SEQUENCE: 119
caagcagaag acggcatacg agatggactt cgaggcgtga ctggagttca gacgtgtgct      60
cttccgatc                                                            69

```
<210> SEQ ID NO 120
<211> LENGTH: 69
<212> TYPE: DNA
<213> ORGANISM: Artificial Sequence
<220> FEATURE:
<223> OTHER INFORMATION: P7 INDEX#062

<400> SEQUENCE: 120
caagcagaag acggcatacg agataaggcc gcgacggtga ctggagttca gacgtgtgct    60
cttccgatc                                                            69

<210> SEQ ID NO 121
<211> LENGTH: 69
<212> TYPE: DNA
<213> ORGANISM: Artificial Sequence
<220> FEATURE:
<223> OTHER INFORMATION: P7 INDEX#063

<400> SEQUENCE: 121
caagcagaag acggcatacg agatggcctt cctccggtga ctggagttca gacgtgtgct    60
cttccgatc                                                            69

<210> SEQ ID NO 122
<211> LENGTH: 69
<212> TYPE: DNA
<213> ORGANISM: Artificial Sequence
<220> FEATURE:
<223> OTHER INFORMATION: P7 INDEX#064

<400> SEQUENCE: 122
caagcagaag acggcatacg agataaggcc ggctgcgtga ctggagttca gacgtgtgct    60
cttccgatc                                                            69

<210> SEQ ID NO 123
<211> LENGTH: 69
<212> TYPE: DNA
<213> ORGANISM: Artificial Sequence
<220> FEATURE:
<223> OTHER INFORMATION: P7 INDEX#065

<400> SEQUENCE: 123
caagcagaag acggcatacg agatggactt ctcttagtga ctggagttca gacgtgtgct    60
cttccgatc                                                            69

<210> SEQ ID NO 124
<211> LENGTH: 69
<212> TYPE: DNA
<213> ORGANISM: Artificial Sequence
<220> FEATURE:
<223> OTHER INFORMATION: P7 INDEX#066

<400> SEQUENCE: 124
caagcagaag acggcatacg agataaggcc gatcatgtga ctggagttca gacgtgtgct    60
cttccgatc                                                            69

<210> SEQ ID NO 125
<211> LENGTH: 69
<212> TYPE: DNA
<213> ORGANISM: Artificial Sequence
<220> FEATURE:
<223> OTHER INFORMATION: P7 INDEX#067

<400> SEQUENCE: 125
```
caagcagaag acggcatacg agatggactt cagaatgtga ctggagttca gacgtgtgct    60
cttccgatc    69

<210> SEQ ID NO 126
<211> LENGTH: 69
<212> TYPE: DNA
<213> ORGANISM: Artificial Sequence
<220> FEATURE:
<223> OTHER INFORMATION: P7 INDEX#068

<400> SEQUENCE: 126
caagcagaag acggcatacg agataaggcc gtagtagtga ctggagttca gacgtgtgct    60
cttccgatc    69

<210> SEQ ID NO 127
<211> LENGTH: 69
<212> TYPE: DNA
<213> ORGANISM: Artificial Sequence
<220> FEATURE:
<223> OTHER INFORMATION: P7 INDEX#069

<400> SEQUENCE: 127
caagcagaag acggcatacg agatggacta ggaccagtga ctggagttca gacgtgtgct    60
cttccgatc    69

<210> SEQ ID NO 128
<211> LENGTH: 69
<212> TYPE: DNA
<213> ORGANISM: Artificial Sequence
<220> FEATURE:
<223> OTHER INFORMATION: P7 INDEX#070

<400> SEQUENCE: 128
caagcagaag acggcatacg agatccggct aatgttgtga ctggagttca gacgtgtgct    60
cttccgatc    69

<210> SEQ ID NO 129
<211> LENGTH: 69
<212> TYPE: DNA
<213> ORGANISM: Artificial Sequence
<220> FEATURE:
<223> OTHER INFORMATION: P7 INDEX#071

<400> SEQUENCE: 129
caagcagaag acggcatacg agatggacta gctggtgtga ctggagttca gacgtgtgct    60
cttccgatc    69

<210> SEQ ID NO 130
<211> LENGTH: 69
<212> TYPE: DNA
<213> ORGANISM: Artificial Sequence
<220> FEATURE:
<223> OTHER INFORMATION: P7 INDEX#072

<400> SEQUENCE: 130
caagcagaag acggcatacg agatccggct atacaagtga ctggagttca gacgtgtgct    60
cttccgatc    69

<210> SEQ ID NO 131
<211> LENGTH: 69
<212> TYPE: DNA
<213> ORGANISM: Artificial Sequence

```
<220> FEATURE:
<223> OTHER INFORMATION: P7 INDEX#073

<400> SEQUENCE: 131
caagcagaag acggcatacg agatggacta gtcaacgtga ctggagttca gacgtgtgct    60
cttccgatc                                                            69

<210> SEQ ID NO 132
<211> LENGTH: 69
<212> TYPE: DNA
<213> ORGANISM: Artificial Sequence
<220> FEATURE:
<223> OTHER INFORMATION: P7 INDEX#074

<400> SEQUENCE: 132
caagcagaag acggcatacg agatccggct acgtgggtga ctggagttca gacgtgtgct    60
cttccgatc                                                            69

<210> SEQ ID NO 133
<211> LENGTH: 69
<212> TYPE: DNA
<213> ORGANISM: Artificial Sequence
<220> FEATURE:
<223> OTHER INFORMATION: P7 INDEX#075

<400> SEQUENCE: 133
caagcagaag acggcatacg agatggacta gagttggtga ctggagttca gacgtgtgct    60
cttccgatc                                                            69

<210> SEQ ID NO 134
<211> LENGTH: 69
<212> TYPE: DNA
<213> ORGANISM: Artificial Sequence
<220> FEATURE:
<223> OTHER INFORMATION: P7 INDEX#076

<400> SEQUENCE: 134
caagcagaag acggcatacg agataaggcg cgcacagtga ctggagttca gacgtgtgct    60
cttccgatc                                                            69

<210> SEQ ID NO 135
<211> LENGTH: 69
<212> TYPE: DNA
<213> ORGANISM: Artificial Sequence
<220> FEATURE:
<223> OTHER INFORMATION: P7 INDEX#077

<400> SEQUENCE: 135
caagcagaag acggcatacg agatggccac agtaccgtga ctggagttca gacgtgtgct    60
cttccgatc                                                            69

<210> SEQ ID NO 136
<211> LENGTH: 69
<212> TYPE: DNA
<213> ORGANISM: Artificial Sequence
<220> FEATURE:
<223> OTHER INFORMATION: P7 INDEX#078

<400> SEQUENCE: 136
caagcagaag acggcatacg agataagggt taatttgtga ctggagttca gacgtgtgct    60
cttccgatc                                                            69
```

```
<210> SEQ ID NO 137
<211> LENGTH: 69
<212> TYPE: DNA
<213> ORGANISM: Artificial Sequence
<220> FEATURE:
<223> OTHER INFORMATION: P7 INDEX#079

<400> SEQUENCE: 137
caagcagaag acggcatacg agatggccac atgcaagtga ctggagttca gacgtgtgct    60
cttccgatc                                                            69

<210> SEQ ID NO 138
<211> LENGTH: 69
<212> TYPE: DNA
<213> ORGANISM: Artificial Sequence
<220> FEATURE:
<223> OTHER INFORMATION: P7 INDEX#080

<400> SEQUENCE: 138
caagcagaag acggcatacg agataagggt tccggggtga ctggagttca gacgtgtgct    60
cttccgatc                                                            69

<210> SEQ ID NO 139
<211> LENGTH: 69
<212> TYPE: DNA
<213> ORGANISM: Artificial Sequence
<220> FEATURE:
<223> OTHER INFORMATION: P7 INDEX#081

<400> SEQUENCE: 139
caagcagaag acggcatacg agatggacac aacgttgtga ctggagttca gacgtgtgct    60
cttccgatc                                                            69

<210> SEQ ID NO 140
<211> LENGTH: 69
<212> TYPE: DNA
<213> ORGANISM: Artificial Sequence
<220> FEATURE:
<223> OTHER INFORMATION: P7 INDEX#082

<400> SEQUENCE: 140
caagcagaag acggcatacg agataagggt tggcccgtga ctggagttca gacgtgtgct    60
cttccgatc                                                            69

<210> SEQ ID NO 141
<211> LENGTH: 69
<212> TYPE: DNA
<213> ORGANISM: Artificial Sequence
<220> FEATURE:
<223> OTHER INFORMATION: P7 INDEX#083

<400> SEQUENCE: 141
caagcagaag acggcatacg agatggacat ggtgtggtga ctggagttca gacgtgtgct    60
cttccgatc                                                            69

<210> SEQ ID NO 142
<211> LENGTH: 69
<212> TYPE: DNA
<213> ORGANISM: Artificial Sequence
<220> FEATURE:
<223> OTHER INFORMATION: P7 INDEX#084

<400> SEQUENCE: 142
```

```
caagcagaag acggcatacg agatccggga accaaagtga ctggagttca gacgtgtgct    60
cttccgatc                                                           69

<210> SEQ ID NO 143
<211> LENGTH: 69
<212> TYPE: DNA
<213> ORGANISM: Artificial Sequence
<220> FEATURE:
<223> OTHER INFORMATION: P7 INDEX#085

<400> SEQUENCE: 143
caagcagaag acggcatacg agatggacat gcacacgtga ctggagttca gacgtgtgct    60
cttccgatc                                                           69

<210> SEQ ID NO 144
<211> LENGTH: 69
<212> TYPE: DNA
<213> ORGANISM: Artificial Sequence
<220> FEATURE:
<223> OTHER INFORMATION: P7 INDEX#086

<400> SEQUENCE: 144
caagcagaag acggcatacg agatccggga attggggtga ctggagttca gacgtgtgct    60
cttccgatc                                                           69

<210> SEQ ID NO 145
<211> LENGTH: 69
<212> TYPE: DNA
<213> ORGANISM: Artificial Sequence
<220> FEATURE:
<223> OTHER INFORMATION: P7 INDEX#087

<400> SEQUENCE: 145
caagcagaag acggcatacg agatggacat gacacagtga ctggagttca gacgtgtgct    60
cttccgatc                                                           69

<210> SEQ ID NO 146
<211> LENGTH: 69
<212> TYPE: DNA
<213> ORGANISM: Artificial Sequence
<220> FEATURE:
<223> OTHER INFORMATION: P7 INDEX#088

<400> SEQUENCE: 146
caagcagaag acggcatacg agatccggga aggtttgtga ctggagttca gacgtgtgct    60
cttccgatc                                                           69

<210> SEQ ID NO 147
<211> LENGTH: 69
<212> TYPE: DNA
<213> ORGANISM: Artificial Sequence
<220> FEATURE:
<223> OTHER INFORMATION: P7 INDEX#089

<400> SEQUENCE: 147
caagcagaag acggcatacg agatggacaa cgtcatgtga ctggagttca gacgtgtgct    60
cttccgatc                                                           69

<210> SEQ ID NO 148
<211> LENGTH: 69
<212> TYPE: DNA
```

<213> ORGANISM: Artificial Sequence
<220> FEATURE:
<223> OTHER INFORMATION: P7 INDEX#090

<400> SEQUENCE: 148
caagcagaag acggcatacg agatccgggt taaggagtga ctggagttca gacgtgtgct    60
cttccgatc                                                             69

<210> SEQ ID NO 149
<211> LENGTH: 69
<212> TYPE: DNA
<213> ORGANISM: Artificial Sequence
<220> FEATURE:
<223> OTHER INFORMATION: P7 INDEX#091

<400> SEQUENCE: 149
caagcagaag acggcatacg agatggacaa ctgacggtga ctggagttca gacgtgtgct    60
cttccgatc                                                             69

<210> SEQ ID NO 150
<211> LENGTH: 69
<212> TYPE: DNA
<213> ORGANISM: Artificial Sequence
<220> FEATURE:
<223> OTHER INFORMATION: P7 INDEX#092

<400> SEQUENCE: 150
caagcagaag acggcatacg agatccgggt tccttcgtga ctggagttca gacgtgtgct    60
cttccgatc                                                             69

<210> SEQ ID NO 151
<211> LENGTH: 69
<212> TYPE: DNA
<213> ORGANISM: Artificial Sequence
<220> FEATURE:
<223> OTHER INFORMATION: P7 INDEX#093

<400> SEQUENCE: 151
caagcagaag acggcatacg agatggccaa cactgcgtga ctggagttca gacgtgtgct    60
cttccgatc                                                             69

<210> SEQ ID NO 152
<211> LENGTH: 69
<212> TYPE: DNA
<213> ORGANISM: Artificial Sequence
<220> FEATURE:
<223> OTHER INFORMATION: P7 INDEX#094

<400> SEQUENCE: 152
caagcagaag acggcatacg agatccgggt tggaaggtga ctggagttca gacgtgtgct    60
cttccgatc                                                             69

<210> SEQ ID NO 153
<211> LENGTH: 69
<212> TYPE: DNA
<213> ORGANISM: Artificial Sequence
<220> FEATURE:
<223> OTHER INFORMATION: P7 INDEX#095

<400> SEQUENCE: 153
caagcagaag acggcatacg agatggctgg tcatacgtga ctggagttca gacgtgtgct    60
cttccgatc                                                             69

<210> SEQ ID NO 154
<211> LENGTH: 69
<212> TYPE: DNA
<213> ORGANISM: Artificial Sequence
<220> FEATURE:
<223> OTHER INFORMATION: P7 INDEX#096

<400> SEQUENCE: 154
caagcagaag acggcatacg agatccgaac cttagggtga ctggagttca gacgtgtgct    60
cttccgatc                                                            69

<210> SEQ ID NO 155
<211> LENGTH: 20
<212> TYPE: DNA
<213> ORGANISM: Artificial Sequence
<220> FEATURE:
<223> OTHER INFORMATION: chr21_gDNA gDNA forward primer

<400> SEQUENCE: 155
ggagcatttt gcggattatt                                                20

<210> SEQ ID NO 156
<211> LENGTH: 20
<212> TYPE: DNA
<213> ORGANISM: Artificial Sequence
<220> FEATURE:
<223> OTHER INFORMATION: chr21_gDNA gDNA reverse primer

<400> SEQUENCE: 156
tgcattggaa gcaagtgaac                                                20

<210> SEQ ID NO 157
<211> LENGTH: 20
<212> TYPE: DNA
<213> ORGANISM: Artificial Sequence
<220> FEATURE:
<223> OTHER INFORMATION: DX_TP53_5 gDNA forward primer

<400> SEQUENCE: 157
tagggcacca ccacactatg                                                20

<210> SEQ ID NO 158
<211> LENGTH: 20
<212> TYPE: DNA
<213> ORGANISM: Artificial Sequence
<220> FEATURE:
<223> OTHER INFORMATION: DX_TP53_5 gDNA reverse primer

<400> SEQUENCE: 158
gtggaaggaa atttgcgtgt                                                20

<210> SEQ ID NO 159
<211> LENGTH: 20
<212> TYPE: DNA
<213> ORGANISM: Artificial Sequence
<220> FEATURE:
<223> OTHER INFORMATION: DX_TP53_8 gDNA forward primer

<400> SEQUENCE: 159
tccagtggtt tcttctttgg                                                20

<210> SEQ ID NO 160
<211> LENGTH: 20
<212> TYPE: DNA

```
<213> ORGANISM: Artificial Sequence
<220> FEATURE:
<223> OTHER INFORMATION: DX_TP53_8 gDNA reverse primer

<400> SEQUENCE: 160
ctttcctagc actgcccaac                                              20

<210> SEQ ID NO 161
<211> LENGTH: 22
<212> TYPE: DNA
<213> ORGANISM: Artificial Sequence
<220> FEATURE:
<223> OTHER INFORMATION: DX_PIK3CA_E545K gDNA forward primer

<400> SEQUENCE: 161
gacaaagaac agctcaaagc aa                                           22

<210> SEQ ID NO 162
<211> LENGTH: 22
<212> TYPE: DNA
<213> ORGANISM: Artificial Sequence
<220> FEATURE:
<223> OTHER INFORMATION: DX_PIK3CA_E545K gDNA reverse primer

<400> SEQUENCE: 162
cctgtgactc catagaaaat ct                                           22

<210> SEQ ID NO 163
<211> LENGTH: 22
<212> TYPE: DNA
<213> ORGANISM: Homo sapiens
<220> FEATURE:
<223> OTHER INFORMATION: DX_ACTB mRNA forward primer

<400> SEQUENCE: 163
tttgtccccc aacttgagat gt                                           22

<210> SEQ ID NO 164
<211> LENGTH: 19
<212> TYPE: DNA
<213> ORGANISM: Homo sapiens

<400> SEQUENCE: 164
ctggctgcct ccacccact                                               19

<210> SEQ ID NO 165
<211> LENGTH: 20
<212> TYPE: DNA
<213> ORGANISM: Homo sapiens

<400> SEQUENCE: 165
tgccagacat caccaggttg                                              20

<210> SEQ ID NO 166
<211> LENGTH: 20
<212> TYPE: DNA
<213> ORGANISM: Homo sapiens

<400> SEQUENCE: 166
gcactgcttg gccctacat                                               20

<210> SEQ ID NO 167
<211> LENGTH: 27
<212> TYPE: DNA
<213> ORGANISM: Homo sapiens
```

```
<400> SEQUENCE: 167
atacatgtgt gggtgctgat aattgtg                                27

<210> SEQ ID NO 168
<211> LENGTH: 26
<212> TYPE: DNA
<213> ORGANISM: Homo sapiens

<400> SEQUENCE: 168
aattgttttc cttttccacc cccaaa                                 26

<210> SEQ ID NO 169
<211> LENGTH: 25
<212> TYPE: DNA
<213> ORGANISM: Homo sapiens

<400> SEQUENCE: 169
tgcttccaca gtaaaatctg aaaaa                                  25

<210> SEQ ID NO 170
<211> LENGTH: 27
<212> TYPE: DNA
<213> ORGANISM: Homo sapiens

<400> SEQUENCE: 170
agactcaagt aaatagaaag gcagctt                                27

<210> SEQ ID NO 171
<211> LENGTH: 24
<212> TYPE: DNA
<213> ORGANISM: Homo sapiens

<400> SEQUENCE: 171
ttgtaaacct cttttgcact ttga                                   24

<210> SEQ ID NO 172
<211> LENGTH: 27
<212> TYPE: DNA
<213> ORGANISM: Homo sapiens

<400> SEQUENCE: 172
ggttgagaaa attgtttaca ggtgctc                                27

<210> SEQ ID NO 173
<211> LENGTH: 22
<212> TYPE: DNA
<213> ORGANISM: Homo sapiens

<400> SEQUENCE: 173
ggccccaatt atccaatagt ct                                     22

<210> SEQ ID NO 174
<211> LENGTH: 27
<212> TYPE: DNA
<213> ORGANISM: Homo sapiens

<400> SEQUENCE: 174
caccaaaacg agtttttatt acttcat                                27

<210> SEQ ID NO 175
<211> LENGTH: 24
<212> TYPE: DNA
```

```
<213> ORGANISM: Homo sapiens

<400> SEQUENCE: 175
ccatcaaggt ccagtggaag ttct                                            24

<210> SEQ ID NO 176
<211> LENGTH: 25
<212> TYPE: DNA
<213> ORGANISM: Homo sapiens

<400> SEQUENCE: 176
ggggtcgctc agtttattgg taaaa                                           25

<210> SEQ ID NO 177
<211> LENGTH: 25
<212> TYPE: DNA
<213> ORGANISM: Homo sapiens

<400> SEQUENCE: 177 gtggttttg ctctcgacag tatcc                                            25

<210> SEQ ID NO 178
<211> LENGTH: 25
<212> TYPE: DNA
<213> ORGANISM: Homo sapiens

<400> SEQUENCE: 178
gcagtgaaga tgaaggcaac aaaat                                           25

<210> SEQ ID NO 179
<211> LENGTH: 22
<212> TYPE: DNA
<213> ORGANISM: Homo sapiens

<400> SEQUENCE: 179
tgtgtatatg ggcgggacgt gt                                              22

<210> SEQ ID NO 180
<211> LENGTH: 25
<212> TYPE: DNA
<213> ORGANISM: Homo sapiens

<400> SEQUENCE: 180
acccctaaac aacagcataa ctcaa                                           25

<210> SEQ ID NO 181
<211> LENGTH: 24
<212> TYPE: DNA
<213> ORGANISM: Homo sapiens

<400> SEQUENCE: 181
ttcctttgtt ccctaagtcc aact                                            24

<210> SEQ ID NO 182
<211> LENGTH: 24
<212> TYPE: DNA
<213> ORGANISM: Homo sapiens

<400> SEQUENCE: 182
atgctcaagg cccttcataa tatc                                            24

<210> SEQ ID NO 183
<211> LENGTH: 12
```

```
<212> TYPE: DNA
<213> ORGANISM: Artificial Sequence
<220> FEATURE:
<223> OTHER INFORMATION: barcode

<400> SEQUENCE: 183
atctagccgg cc                                                             12

<210> SEQ ID NO 184
<211> LENGTH: 12
<212> TYPE: DNA
<213> ORGANISM: Artificial Sequence
<220> FEATURE:
<223> OTHER INFORMATION: barcode

<400> SEQUENCE: 184
tatctcttcc tt                                                             12

<210> SEQ ID NO 185
<211> LENGTH: 12
<212> TYPE: DNA
<213> ORGANISM: Artificial Sequence
<220> FEATURE:
<223> OTHER INFORMATION: barcode

<400> SEQUENCE: 185
tagatgccgt cc                                                             12

<210> SEQ ID NO 186
<211> LENGTH: 12
<212> TYPE: DNA
<213> ORGANISM: Artificial Sequence
<220> FEATURE:
<223> OTHER INFORMATION: barcode

<400> SEQUENCE: 186
cgctccttcc tt                                                             12

<210> SEQ ID NO 187
<211> LENGTH: 12
<212> TYPE: DNA
<213> ORGANISM: Artificial Sequence
<220> FEATURE:
<223> OTHER INFORMATION: barcode

<400> SEQUENCE: 187
cgagcgccgt cc                                                             12

<210> SEQ ID NO 188
<211> LENGTH: 12
<212> TYPE: DNA
<213> ORGANISM: Artificial Sequence
<220> FEATURE:
<223> OTHER INFORMATION: barcode

<400> SEQUENCE: 188
tcgagagtcc gg                                                             12

<210> SEQ ID NO 189
<211> LENGTH: 12
<212> TYPE: DNA
<213> ORGANISM: Artificial Sequence
<220> FEATURE:
<223> OTHER INFORMATION: barcode

<400> SEQUENCE: 189
```

```
gctcggccgg cc                                              12

<210> SEQ ID NO 190
<211> LENGTH: 12
<212> TYPE: DNA
<213> ORGANISM: Artificial Sequence
<220> FEATURE:
<223> OTHER INFORMATION: barcode

<400> SEQUENCE: 190
agctcagtcc gg                                              12

<210> SEQ ID NO 191
<211> LENGTH: 12
<212> TYPE: DNA
<213> ORGANISM: Artificial Sequence
<220> FEATURE:
<223> OTHER INFORMATION: barcode

<400> SEQUENCE: 191
actgccgcgt cc                                              12

<210> SEQ ID NO 192
<211> LENGTH: 12
<212> TYPE: DNA
<213> ORGANISM: Artificial Sequence
<220> FEATURE:
<223> OTHER INFORMATION: barcode

<400> SEQUENCE: 192
ttacttctcc gg                                              12

<210> SEQ ID NO 193
<211> LENGTH: 12
<212> TYPE: DNA
<213> ORGANISM: Artificial Sequence
<220> FEATURE:
<223> OTHER INFORMATION: barcode

<400> SEQUENCE: 193
tgacgcgcgg cc                                              12

<210> SEQ ID NO 194
<211> LENGTH: 12
<212> TYPE: DNA
<213> ORGANISM: Artificial Sequence
<220> FEATURE:
<223> OTHER INFORMATION: barcode

<400> SEQUENCE: 194
aatgatctcc gg                                              12

<210> SEQ ID NO 195
<211> LENGTH: 12
<212> TYPE: DNA
<213> ORGANISM: Artificial Sequence
<220> FEATURE:
<223> OTHER INFORMATION: barcode

<400> SEQUENCE: 195
aagcgtacgt cc                                              12

<210> SEQ ID NO 196
<211> LENGTH: 12
<212> TYPE: DNA
<213> ORGANISM: Artificial Sequence
```

```
<220> FEATURE:
<223> OTHER INFORMATION: barcode

<400> SEQUENCE: 196
ttatcagtcc tt                                                              12

<210> SEQ ID NO 197
<211> LENGTH: 12
<212> TYPE: DNA
<213> ORGANISM: Artificial Sequence
<220> FEATURE:
<223> OTHER INFORMATION: barcode

<400> SEQUENCE: 197
gtcatcgcgt cc                                                              12

<210> SEQ ID NO 198
<211> LENGTH: 12
<212> TYPE: DNA
<213> ORGANISM: Artificial Sequence
<220> FEATURE:
<223> OTHER INFORMATION: barcode

<400> SEQUENCE: 198
ccgtctctcc gg                                                              12

<210> SEQ ID NO 199
<211> LENGTH: 12
<212> TYPE: DNA
<213> ORGANISM: Artificial Sequence
<220> FEATURE:
<223> OTHER INFORMATION: barcode

<400> SEQUENCE: 199
ttcgctacgt cc                                                              12

<210> SEQ ID NO 200
<211> LENGTH: 12
<212> TYPE: DNA
<213> ORGANISM: Artificial Sequence
<220> FEATURE:
<223> OTHER INFORMATION: barcode

<400> SEQUENCE: 200
acgctcttcc gg                                                              12

<210> SEQ ID NO 201
<211> LENGTH: 12
<212> TYPE: DNA
<213> ORGANISM: Artificial Sequence
<220> FEATURE:
<223> OTHER INFORMATION: barcode

<400> SEQUENCE: 201
cagtacgcgg cc                                                              12

<210> SEQ ID NO 202
<211> LENGTH: 12
<212> TYPE: DNA
<213> ORGANISM: Artificial Sequence
<220> FEATURE:
<223> OTHER INFORMATION: barcode

<400> SEQUENCE: 202
gtactgatcc tt                                                              12
```

-continued

```
<210> SEQ ID NO 203
<211> LENGTH: 12
<212> TYPE: DNA
<213> ORGANISM: Artificial Sequence
<220> FEATURE:
<223> OTHER INFORMATION: barcode

<400> SEQUENCE: 203
ggatatacgg cc                                                               12

<210> SEQ ID NO 204
<211> LENGTH: 12
<212> TYPE: DNA
<213> ORGANISM: Artificial Sequence
<220> FEATURE:
<223> OTHER INFORMATION: barcode

<400> SEQUENCE: 204
catagcttcc gg                                                               12

<210> SEQ ID NO 205
<211> LENGTH: 12
<212> TYPE: DNA
<213> ORGANISM: Artificial Sequence
<220> FEATURE:
<223> OTHER INFORMATION: barcode

<400> SEQUENCE: 205
gaggcatcgg cc                                                               12

<210> SEQ ID NO 206
<211> LENGTH: 12
<212> TYPE: DNA
<213> ORGANISM: Artificial Sequence
<220> FEATURE:
<223> OTHER INFORMATION: barcode

<400> SEQUENCE: 206
ataaggatcc gg                                                               12

<210> SEQ ID NO 207
<211> LENGTH: 12
<212> TYPE: DNA
<213> ORGANISM: Artificial Sequence
<220> FEATURE:
<223> OTHER INFORMATION: barcode

<400> SEQUENCE: 207
ctccgatcgt cc                                                               12

<210> SEQ ID NO 208
<211> LENGTH: 12
<212> TYPE: DNA
<213> ORGANISM: Artificial Sequence
<220> FEATURE:
<223> OTHER INFORMATION: barcode

<400> SEQUENCE: 208
tattcgatcc gg                                                               12

<210> SEQ ID NO 209
<211> LENGTH: 12
<212> TYPE: DNA
<213> ORGANISM: Artificial Sequence
<220> FEATURE:
<223> OTHER INFORMATION: barcode
```

```
<400> SEQUENCE: 209
tcttaatcgt cc                                                    12

<210> SEQ ID NO 210
<211> LENGTH: 12
<212> TYPE: DNA
<213> ORGANISM: Artificial Sequence
<220> FEATURE:
<223> OTHER INFORMATION: barcode

<400> SEQUENCE: 210
cgcctgatcc gg                                                    12

<210> SEQ ID NO 211
<211> LENGTH: 12
<212> TYPE: DNA
<213> ORGANISM: Artificial Sequence
<220> FEATURE:
<223> OTHER INFORMATION: barcode

<400> SEQUENCE: 211
agaatatcgt cc                                                    12

<210> SEQ ID NO 212
<211> LENGTH: 12
<212> TYPE: DNA
<213> ORGANISM: Artificial Sequence
<220> FEATURE:
<223> OTHER INFORMATION: barcode

<400> SEQUENCE: 212
gcggagatcc gg                                                    12

<210> SEQ ID NO 213
<211> LENGTH: 12
<212> TYPE: DNA
<213> ORGANISM: Artificial Sequence
<220> FEATURE:
<223> OTHER INFORMATION: barcode

<400> SEQUENCE: 213
catggccggt cc                                                    12

<210> SEQ ID NO 214
<211> LENGTH: 12
<212> TYPE: DNA
<213> ORGANISM: Artificial Sequence
<220> FEATURE:
<223> OTHER INFORMATION: barcode

<400> SEQUENCE: 214
gtcacgtacc tt                                                    12

<210> SEQ ID NO 215
<211> LENGTH: 12
<212> TYPE: DNA
<213> ORGANISM: Artificial Sequence
<220> FEATURE:
<223> OTHER INFORMATION: barcode

<400> SEQUENCE: 215
tgcaaccggt cc                                                    12

<210> SEQ ID NO 216
```

```
<211> LENGTH: 12
<212> TYPE: DNA
<213> ORGANISM: Artificial Sequence
<220> FEATURE:
<223> OTHER INFORMATION: barcode

<400> SEQUENCE: 216
cctgttgacc gg                                                          12

<210> SEQ ID NO 217
<211> LENGTH: 12
<212> TYPE: DNA
<213> ORGANISM: Artificial Sequence
<220> FEATURE:
<223> OTHER INFORMATION: barcode

<400> SEQUENCE: 217
agcccaaggt cc                                                          12

<210> SEQ ID NO 218
<211> LENGTH: 12
<212> TYPE: DNA
<213> ORGANISM: Artificial Sequence
<220> FEATURE:
<223> OTHER INFORMATION: barcode

<400> SEQUENCE: 218
gcttggtacc gg                                                          12

<210> SEQ ID NO 219
<211> LENGTH: 12
<212> TYPE: DNA
<213> ORGANISM: Artificial Sequence
<220> FEATURE:
<223> OTHER INFORMATION: barcode

<400> SEQUENCE: 219
tcgggaaggt cc                                                          12

<210> SEQ ID NO 220
<211> LENGTH: 12
<212> TYPE: DNA
<213> ORGANISM: Artificial Sequence
<220> FEATURE:
<223> OTHER INFORMATION: barcode

<400> SEQUENCE: 220
cgaacgtacc gg                                                          12

<210> SEQ ID NO 221
<211> LENGTH: 12
<212> TYPE: DNA
<213> ORGANISM: Artificial Sequence
<220> FEATURE:
<223> OTHER INFORMATION: barcode

<400> SEQUENCE: 221
gatttaaggg cc                                                          12

<210> SEQ ID NO 222
<211> LENGTH: 12
<212> TYPE: DNA
<213> ORGANISM: Artificial Sequence
<220> FEATURE:
<223> OTHER INFORMATION: barcode

<400> SEQUENCE: 222
```
agaactgacc tt                                              12

<210> SEQ ID NO 223
<211> LENGTH: 12
<212> TYPE: DNA
<213> ORGANISM: Artificial Sequence
<220> FEATURE:
<223> OTHER INFORMATION: barcode

<400> SEQUENCE: 223
ccgccttggt cc                                              12

<210> SEQ ID NO 224
<211> LENGTH: 12
<212> TYPE: DNA
<213> ORGANISM: Artificial Sequence
<220> FEATURE:
<223> OTHER INFORMATION: barcode

<400> SEQUENCE: 224
tgatgcaacc gg                                              12

<210> SEQ ID NO 225
<211> LENGTH: 12
<212> TYPE: DNA
<213> ORGANISM: Artificial Sequence
<220> FEATURE:
<223> OTHER INFORMATION: barcode

<400> SEQUENCE: 225
ggcggttggg cc                                              12

<210> SEQ ID NO 226
<211> LENGTH: 12
<212> TYPE: DNA
<213> ORGANISM: Artificial Sequence
<220> FEATURE:
<223> OTHER INFORMATION: barcode

<400> SEQUENCE: 226
actaccaacc gg                                              12

<210> SEQ ID NO 227
<211> LENGTH: 12
<212> TYPE: DNA
<213> ORGANISM: Artificial Sequence
<220> FEATURE:
<223> OTHER INFORMATION: barcode

<400> SEQUENCE: 227
aataattggt cc                                              12

<210> SEQ ID NO 228
<211> LENGTH: 12
<212> TYPE: DNA
<213> ORGANISM: Artificial Sequence
<220> FEATURE:
<223> OTHER INFORMATION: barcode

<400> SEQUENCE: 228
gtcgtcaacc gg                                              12

<210> SEQ ID NO 229
<211> LENGTH: 12
<212> TYPE: DNA

```
<213> ORGANISM: Artificial Sequence
<220> FEATURE:
<223> OTHER INFORMATION: barcode

<400> SEQUENCE: 229
aaatctcagg cc                                                              12

<210> SEQ ID NO 230
<211> LENGTH: 12
<212> TYPE: DNA
<213> ORGANISM: Artificial Sequence
<220> FEATURE:
<223> OTHER INFORMATION: barcode

<400> SEQUENCE: 230
gtgcgcggcc gg                                                              12

<210> SEQ ID NO 231
<211> LENGTH: 12
<212> TYPE: DNA
<213> ORGANISM: Artificial Sequence
<220> FEATURE:
<223> OTHER INFORMATION: barcode

<400> SEQUENCE: 231
tttagtcagt cc                                                              12

<210> SEQ ID NO 232
<211> LENGTH: 12
<212> TYPE: DNA
<213> ORGANISM: Artificial Sequence
<220> FEATURE:
<223> OTHER INFORMATION: barcode

<400> SEQUENCE: 232
cacgccggcc gg                                                              12

<210> SEQ ID NO 233
<211> LENGTH: 12
<212> TYPE: DNA
<213> ORGANISM: Artificial Sequence
<220> FEATURE:
<223> OTHER INFORMATION: barcode

<400> SEQUENCE: 233
cccgatcagt cc                                                              12

<210> SEQ ID NO 234
<211> LENGTH: 12
<212> TYPE: DNA
<213> ORGANISM: Artificial Sequence
<220> FEATURE:
<223> OTHER INFORMATION: barcode

<400> SEQUENCE: 234
tgtatcggcc gg                                                              12

<210> SEQ ID NO 235
<211> LENGTH: 12
<212> TYPE: DNA
<213> ORGANISM: Artificial Sequence
<220> FEATURE:
<223> OTHER INFORMATION: barcode

<400> SEQUENCE: 235
ctttcagagt cc                                                              12
```

<210> SEQ ID NO 236
<211> LENGTH: 12
<212> TYPE: DNA
<213> ORGANISM: Artificial Sequence
<220> FEATURE:
<223> OTHER INFORMATION: barcode

<400> SEQUENCE: 236
taccggcgcc gg                                                          12

<210> SEQ ID NO 237
<211> LENGTH: 12
<212> TYPE: DNA
<213> ORGANISM: Artificial Sequence
<220> FEATURE:
<223> OTHER INFORMATION: barcode

<400> SEQUENCE: 237
gaaagagagt cc                                                          12

<210> SEQ ID NO 238
<211> LENGTH: 12
<212> TYPE: DNA
<213> ORGANISM: Artificial Sequence
<220> FEATURE:
<223> OTHER INFORMATION: barcode

<400> SEQUENCE: 238
ctggctagcc tt                                                          12

<210> SEQ ID NO 239
<211> LENGTH: 12
<212> TYPE: DNA
<213> ORGANISM: Artificial Sequence
<220> FEATURE:
<223> OTHER INFORMATION: barcode

<400> SEQUENCE: 239
agggaagagg cc                                                          12

<210> SEQ ID NO 240
<211> LENGTH: 12
<212> TYPE: DNA
<213> ORGANISM: Artificial Sequence
<220> FEATURE:
<223> OTHER INFORMATION: barcode

<400> SEQUENCE: 240
gaccgtagcc tt                                                          12

<210> SEQ ID NO 241
<211> LENGTH: 12
<212> TYPE: DNA
<213> ORGANISM: Artificial Sequence
<220> FEATURE:
<223> OTHER INFORMATION: barcode

<400> SEQUENCE: 241
tccctagagt cc                                                          12

<210> SEQ ID NO 242
<211> LENGTH: 12
<212> TYPE: DNA
<213> ORGANISM: Artificial Sequence
<220> FEATURE:

-continued

<223> OTHER INFORMATION: barcode

<400> SEQUENCE: 242
agttatagcc tt                                                          12

<210> SEQ ID NO 243
<211> LENGTH: 12
<212> TYPE: DNA
<213> ORGANISM: Artificial Sequence
<220> FEATURE:
<223> OTHER INFORMATION: barcode

<400> SEQUENCE: 243
gcctcgaagt cc                                                          12

<210> SEQ ID NO 244
<211> LENGTH: 12
<212> TYPE: DNA
<213> ORGANISM: Artificial Sequence
<220> FEATURE:
<223> OTHER INFORMATION: barcode

<400> SEQUENCE: 244
cgtcgcggcc tt                                                          12

<210> SEQ ID NO 245
<211> LENGTH: 12
<212> TYPE: DNA
<213> ORGANISM: Artificial Sequence
<220> FEATURE:
<223> OTHER INFORMATION: barcode

<400> SEQUENCE: 245
cggaggaagg cc                                                          12

<210> SEQ ID NO 246
<211> LENGTH: 12
<212> TYPE: DNA
<213> ORGANISM: Artificial Sequence
<220> FEATURE:
<223> OTHER INFORMATION: barcode

<400> SEQUENCE: 246
gcagccggcc tt                                                          12

<210> SEQ ID NO 247
<211> LENGTH: 12
<212> TYPE: DNA
<213> ORGANISM: Artificial Sequence
<220> FEATURE:
<223> OTHER INFORMATION: barcode

<400> SEQUENCE: 247
taagagaagt cc                                                          12

<210> SEQ ID NO 248
<211> LENGTH: 12
<212> TYPE: DNA
<213> ORGANISM: Artificial Sequence
<220> FEATURE:
<223> OTHER INFORMATION: barcode

<400> SEQUENCE: 248
atgatcggcc tt                                                          12

```
<210> SEQ ID NO 249
<211> LENGTH: 12
<212> TYPE: DNA
<213> ORGANISM: Artificial Sequence
<220> FEATURE:
<223> OTHER INFORMATION: barcode

<400> SEQUENCE: 249
attctgaagt cc                                                              12

<210> SEQ ID NO 250
<211> LENGTH: 12
<212> TYPE: DNA
<213> ORGANISM: Artificial Sequence
<220> FEATURE:
<223> OTHER INFORMATION: barcode

<400> SEQUENCE: 250
tactacggcc tt                                                              12

<210> SEQ ID NO 251
<211> LENGTH: 12
<212> TYPE: DNA
<213> ORGANISM: Artificial Sequence
<220> FEATURE:
<223> OTHER INFORMATION: barcode

<400> SEQUENCE: 251
tggtcctagt cc                                                              12

<210> SEQ ID NO 252
<211> LENGTH: 12
<212> TYPE: DNA
<213> ORGANISM: Artificial Sequence
<220> FEATURE:
<223> OTHER INFORMATION: barcode

<400> SEQUENCE: 252
aacattagcc gg                                                              12

<210> SEQ ID NO 253
<211> LENGTH: 12
<212> TYPE: DNA
<213> ORGANISM: Artificial Sequence
<220> FEATURE:
<223> OTHER INFORMATION: barcode

<400> SEQUENCE: 253
accagctagt cc                                                              12

<210> SEQ ID NO 254
<211> LENGTH: 12
<212> TYPE: DNA
<213> ORGANISM: Artificial Sequence
<220> FEATURE:
<223> OTHER INFORMATION: barcode

<400> SEQUENCE: 254
ttgtatagcc gg                                                              12

<210> SEQ ID NO 255
<211> LENGTH: 12
<212> TYPE: DNA
<213> ORGANISM: Artificial Sequence
<220> FEATURE:
<223> OTHER INFORMATION: barcode
```

<400> SEQUENCE: 255
gttgactagt cc                                                    12

<210> SEQ ID NO 256
<211> LENGTH: 12
<212> TYPE: DNA
<213> ORGANISM: Artificial Sequence
<220> FEATURE:
<223> OTHER INFORMATION: barcode

<400> SEQUENCE: 256
ccacgtagcc gg                                                    12

<210> SEQ ID NO 257
<211> LENGTH: 12
<212> TYPE: DNA
<213> ORGANISM: Artificial Sequence
<220> FEATURE:
<223> OTHER INFORMATION: barcode

<400> SEQUENCE: 257
caactctagt cc                                                    12

<210> SEQ ID NO 258
<211> LENGTH: 12
<212> TYPE: DNA
<213> ORGANISM: Artificial Sequence
<220> FEATURE:
<223> OTHER INFORMATION: barcode

<400> SEQUENCE: 258
tgtgcgcgcc tt                                                    12

<210> SEQ ID NO 259
<211> LENGTH: 12
<212> TYPE: DNA
<213> ORGANISM: Artificial Sequence
<220> FEATURE:
<223> OTHER INFORMATION: barcode

<400> SEQUENCE: 259
ggtactgtgg cc                                                    12

<210> SEQ ID NO 260
<211> LENGTH: 12
<212> TYPE: DNA
<213> ORGANISM: Artificial Sequence
<220> FEATURE:
<223> OTHER INFORMATION: barcode

<400> SEQUENCE: 260
aaattaaccc tt                                                    12

<210> SEQ ID NO 261
<211> LENGTH: 12
<212> TYPE: DNA
<213> ORGANISM: Artificial Sequence
<220> FEATURE:
<223> OTHER INFORMATION: barcode

<400> SEQUENCE: 261
ttgcatgtgg cc                                                    12

<210> SEQ ID NO 262
<211> LENGTH: 12

```
<212> TYPE: DNA
<213> ORGANISM: Artificial Sequence
<220> FEATURE:
<223> OTHER INFORMATION: barcode

<400> SEQUENCE: 262
cccggaaccc tt                                                     12

<210> SEQ ID NO 263
<211> LENGTH: 12
<212> TYPE: DNA
<213> ORGANISM: Artificial Sequence
<220> FEATURE:
<223> OTHER INFORMATION: barcode

<400> SEQUENCE: 263
aacgttgtgt cc                                                     12

<210> SEQ ID NO 264
<211> LENGTH: 12
<212> TYPE: DNA
<213> ORGANISM: Artificial Sequence
<220> FEATURE:
<223> OTHER INFORMATION: barcode

<400> SEQUENCE: 264
gggccaaccc tt                                                     12

<210> SEQ ID NO 265
<211> LENGTH: 12
<212> TYPE: DNA
<213> ORGANISM: Artificial Sequence
<220> FEATURE:
<223> OTHER INFORMATION: barcode

<400> SEQUENCE: 265
cacaccatgt cc                                                     12

<210> SEQ ID NO 266
<211> LENGTH: 12
<212> TYPE: DNA
<213> ORGANISM: Artificial Sequence
<220> FEATURE:
<223> OTHER INFORMATION: barcode

<400> SEQUENCE: 266
tttggttccc gg                                                     12

<210> SEQ ID NO 267
<211> LENGTH: 12
<212> TYPE: DNA
<213> ORGANISM: Artificial Sequence
<220> FEATURE:
<223> OTHER INFORMATION: barcode

<400> SEQUENCE: 267
gtgtgcatgt cc                                                     12

<210> SEQ ID NO 268
<211> LENGTH: 12
<212> TYPE: DNA
<213> ORGANISM: Artificial Sequence
<220> FEATURE:
<223> OTHER INFORMATION: barcode

<400> SEQUENCE: 268
```
cccaattccc gg                                                                          12

<210> SEQ ID NO 269
<211> LENGTH: 12
<212> TYPE: DNA
<213> ORGANISM: Artificial Sequence
<220> FEATURE:
<223> OTHER INFORMATION: barcode

<400> SEQUENCE: 269
tgtgtcatgt cc                                                                          12

<210> SEQ ID NO 270
<211> LENGTH: 12
<212> TYPE: DNA
<213> ORGANISM: Artificial Sequence
<220> FEATURE:
<223> OTHER INFORMATION: barcode

<400> SEQUENCE: 270
aaaccttccc gg                                                                          12

<210> SEQ ID NO 271
<211> LENGTH: 12
<212> TYPE: DNA
<213> ORGANISM: Artificial Sequence
<220> FEATURE:
<223> OTHER INFORMATION: barcode

<400> SEQUENCE: 271
atgacgttgt cc                                                                          12

<210> SEQ ID NO 272
<211> LENGTH: 12
<212> TYPE: DNA
<213> ORGANISM: Artificial Sequence
<220> FEATURE:
<223> OTHER INFORMATION: barcode

<400> SEQUENCE: 272
tccttaaccc gg                                                                          12

<210> SEQ ID NO 273
<211> LENGTH: 12
<212> TYPE: DNA
<213> ORGANISM: Artificial Sequence
<220> FEATURE:
<223> OTHER INFORMATION: barcode

<400> SEQUENCE: 273
cgtcagttgt cc                                                                          12

<210> SEQ ID NO 274
<211> LENGTH: 12
<212> TYPE: DNA
<213> ORGANISM: Artificial Sequence
<220> FEATURE:
<223> OTHER INFORMATION: barcode

<400> SEQUENCE: 274
gaaggaaccc gg                                                                          12

<210> SEQ ID NO 275
<211> LENGTH: 12
<212> TYPE: DNA
<213> ORGANISM: Artificial Sequence

```
<220> FEATURE:
<223> OTHER INFORMATION: barcode

<400> SEQUENCE: 275
gcagtgttgg cc                                                        12

<210> SEQ ID NO 276
<211> LENGTH: 12
<212> TYPE: DNA
<213> ORGANISM: Artificial Sequence
<220> FEATURE:
<223> OTHER INFORMATION: barcode

<400> SEQUENCE: 276
cttccaaccc gg                                                        12

<210> SEQ ID NO 277
<211> LENGTH: 12
<212> TYPE: DNA
<213> ORGANISM: Artificial Sequence
<220> FEATURE:
<223> OTHER INFORMATION: barcode

<400> SEQUENCE: 277
gtatgaccag cc                                                        12

<210> SEQ ID NO 278
<211> LENGTH: 12
<212> TYPE: DNA
<213> ORGANISM: Artificial Sequence
<220> FEATURE:
<223> OTHER INFORMATION: barcode

<400> SEQUENCE: 278
cctaaggttc gg                                                        12
```

GENOMICS-BASED IDENTIFICATION AND CHARACTERIZATION OF RARE CELL TYPES

This application incorporates by reference the contents of a 54.2 kb text file created on Jun. 28, 2021 and named "00899500033_sequencelisting.txt," which is the sequence listing for this application.

Each reference cited in this disclosure is incorporated herein in its entirety.

TECHNICAL FIELD

This disclosure relates generally to the identification and characterization of rare cell types.

BACKGROUND

Circulating Tumor Cells (CTC) have been reported in patients with a wide variety of cancer types and stages of disease, and their detection and analyses holds great potential as a non-invasive approach to guide the diagnosis and treatment of solid tumors in the clinic. However, significant technical hurdles continue to impede the development and adoption of CTC tests in routine medical practice. There exists a need for methods that provide highly sensitive and accurate detection and characterization of CTCs, as well as other rare cell types, in a liquid sample.

BRIEF DESCRIPTION OF THE DRAWINGS

FIG. 5B, CDH1) in NGS libraries. Data are shown for libraries generated from blood only, MCF7 only and blood samples spiked with varying levels of MCF7. Each input sample consisted of total RNA and gDNA as described in Example 5.

FIG. 6A, MCF7 only. FIG. 6B, 8% MCF7. FIG. 6C, 4% MCF7. FIG. 6D, 2% MCF7. FIG. 6E, 1% MCF7. FIG. 6F, 0% MCF7.

DETAILED DESCRIPTION

Figure 1:
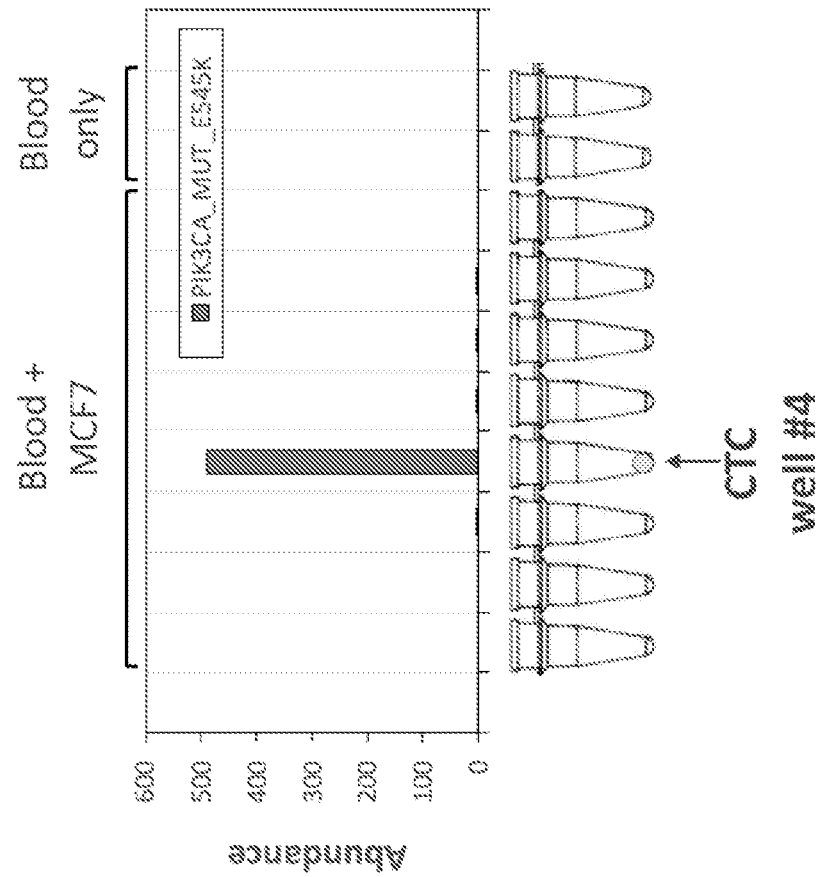
FIG. 1 shows mutation abundance in a subset of wells from the specimen spiked with MCF7 cells diluted 1:10,000 before arraying into a microplate. Each bar in the graph represents data from one well. The figure shows high mutation signal in Well #4, indicating the presence of one or more MCF7 cells.

This disclosure provides methods that address key technical bottlenecks in each of the three pillars of rare cell analysis: enrichment, identification, and classification. These methods are described below with respect to CTCs, but can be readily applied to other rare cell types, such as circulating epithelial cells (CECs), stem cells, progenitor cells, and rare immune cells (e.g., $PD1^+$ $CD8^+$ $IFN\gamma^+$ $TIM3^+$ $LAG3^+$ positive T cells), circulating endothelial cells (CECs), white blood cells in emboli, cancer stem cells, activated or infected cells (e.g., activated or infected blood cells), and fetal cells.

The disclosed methods can be used in liquid biopsies of fluids (e.g., blood, cerebrospinal fluid, urine) for a variety of purposes. These include, but are not limited to, screening for and diagnosing disease, identifying an appropriate therapy (e.g., as a companion diagnostic), monitoring a response to a therapy, and detecting drug resistance.

1. Enrichment

It is often useful to enrich a biological sample for the presence of a rare cell type. For example, cells originating from solid tumors are an extremely rare component of blood even in patients with late-stage metastatic disease. Five milliliters of whole blood typically contain 25 billion erythrocytes, 1.5 billion platelets and 25 million leukocytes. CTCs, in contrast, can be present at 10 or fewer cells in the same volume of blood. To address this problem, current approaches to CTC analysis employ strategies to increase tumor representation relative to non-tumor background cells.

Conventional enrichment approaches for CTCs rely on biological properties and/or physical properties of CTCs. For example, antibody-based positive selection of cells expressing Epithelial Cell Adhesion Molecule (EPCAM), a surface protein present on many solid tumor cells, is frequently used to enrich the number of CTCs in a sample. This approach can result in cellular fractions with very high tumor content (90% or greater). This comes at a high cost, however, because the expression of EPCAM and similar markers can vary widely within a given patient due to tumor heterogeneity and across different cancer types. Tumor cells often escape capture, which introduces biases that can lower assay sensitivity dramatically. Another drawback of positive selection is that these methods are frequently optimized for single cell enrichment and, as a result, fail to account for clusters of 2 or more tumor cells. Clusters represent a class of CTCs that is increasingly recognized as an important driver of tumor progression and metastases.

Physical properties (e.g., tumor cell mass, tumor cell size, tumor cell shape) and negative selection of leukocyte-specific surface markers such as CD45, impart less bias during enrichment, but they produce CTC fractions that contain much higher levels of non-tumor blood cells when compared to positive selection schemes, making downstream tumor identification and analysis technically problematic.

Counterintuitively, in the disclosed methods, enrichment bias is mitigated by applying less stringency during the CTC enrichment. Because the disclosed methods do not depend on detecting one or two protein markers, CTCs—and CTC clusters—with more diverse molecular profiles and from more cancer types are recovered. Clusters can be distinguished from single CTCs microscopically. In embodiments of the disclosed methods, cell lysates from a biological sample are physically divided into individual wells of a microplate after enrichment. This permits analysis to be carried out in each well independently, which dramatically increases the signal-to-noise ratio in CTC-containing wells. For example, if a post-enrichment specimen containing one CTC and 10,000 non-tumor cells is dispensed into wells of a 96-well plate, there will be on average 104 total cells per well. Tumor representation, in this case, increases from 0.01% in the starting sample to 1% in a single CTC containing well.

2. Identification

With conventional approaches, CTCs are distinguished from non-tumor cells by microscopic detection of a few protein markers using antibodies. Cells are commonly classified as CTCs if they are positive for EPCAM and cytokeratin proteins and negative for the leukocyte-specific protein CD45. As with enrichment, variations in expression due to tumor heterogeneity and cancer type limit the sensitivity and robustness of these markers for CTC identification. Moreover, they rely on subjective image analysis calls that can lead to misclassification of cells. These drawbacks can reduce the fidelity of assay performance and limit their application in the clinic.

The disclosed methods overcome these limitations by leveraging the exquisite specificity of cancer genomic alterations as identifying markers for CTCs; i.e., the methods use genomics for CTC identification. For example, cell samples (e.g., 100-200 total cells per well) arrayed in plates following an enrichment step can be assessed for one or more mutations in selected cancer driver genes using nucleic acid sequencing methods (e.g., next-generation sequencing, NGS). Wells in which a mutation is detected contain at least one CTC, while wells in which no mutations contain only non-tumor cells. Downstream CTC classification efforts can then be focused on mutation-positive CTC wells. See, for example, Example 3.

Construction of Sequencing Libraries

In constructing an NGS sequencing library, a molecular barcode specific for each well is incorporated into genomic DNA constructs and/or cDNA constructs. The samples can then be pooled prior to sequencing because the identity of the barcode permits the identification of individual wells after sequencing. This allows CTC identification and CTC classification to be integrated during data generation. Moreover, by the choice of target sequences amplified by the primers, the content of the sequencing libraries is programmable. In some embodiments, a primer pool can comprise one or more primers specific for one or more biological markers (e.g., as a drug resistance marker, a tissue-specific marker, a drug response marker, a molecular subtyping marker).

Sequencing libraries for use in the disclosed methods can be gDNA libraries, cDNA libraries, or libraries containing both gDNA and cDNA. In some embodiments the disclosed methods use a target RT-PCR sample preparation method in which gDNA and mRNA targets are co-amplified for analysis by NGS. Two types of primers provided in this disclosure are used: (1) universal NGS primers and (2) target-specific primers (TSPs).

Lysed cells are reverse transcribed using an oligo d(T) primer to generate cDNA. Multiplex PCR is then used to amplify a defined set of transcripts and gDNA targets using a pool of TSPs. Universal sites that facilitate NGS are added in two steps. First, a 15-16 nucleotide sequence representing a portion of the universal NGS site is added to the 5' terminus of oligo d(T) and TSPs during primer synthesis. These tail sequences are introduced into the library during the reverse transcription and multiplex PCR reactions. The 5' tails are then extended via a second round of PCR using primers containing the full-length universal NGS sequences.

3. Classification

The scope and clinical utility of CTC profiling has been limited largely by the reliance on microscopy and high content imaging to characterize CTCs. Consequently, clinical tests have focused on simple metrics and biomarker readouts. CTC enumeration as a prognostic indicator or single protein markers to guide treatment in selected cancer types are a few examples of existing clinical applications.

The disclosed methods use genomics to expand the size and complexity of CTC biomarkers to address a wide range of clinical applications. The ability of these methods to assess both DNA alterations and RNA abundance in a single assay enables applications such as tissue-of-origin classification, disease prognosis, tumor-subtyping to guide treatment, characterization of mechanisms of resistance, and monitoring of disease status and recurrence following treatment. The examples below demonstrate that the disclosed methods preserve the integrity of RNA abundance and mutational status when generated from low inputs (10-100 cells). Using the disclosed methods, RNA markers that are highly expressed in tumors and weakly expressed in leukocytes can be easily detected when tumor content is 1% or lower.

Example 1. CTC Enrichment, Array Allocation, and Lysis

Blood Collection. Whole blood was collected from into BCT tubes (STRECK®) and stored for 48 hours at room temperature until processing.

Red Blood Cell (RBC) Lysis. Each blood sample was added to 40 mL of cold Ammonium Chloride Solution (STEMCELL™ Technologies) in a 50 mL FALCON® conical centrifuge tube, mixed by inverting the tube several times and incubated on ice for 10 minutes. Each tube was then centrifuged at 800 relative centrifugal force (RCF) for 10 minutes in a fixed rotor centrifuge at room temperature. Supernatant was decanted, and pellets were resuspended in 15 mL of Dulbecco's Phosphate-Buffered Saline (DPBS)+ 2% fetal bovine serum (FBS) before centrifuging at 200 RCF for 10 minutes. Cells were washed a second time and resuspended in 5 mL of DPBS+2% FBS.

Density Gradient Separation. Five mL of cell resuspension from the RBC lysis procedure were added to 5 mL of room temperature Wash Buffer (PLURISELECT®Life Science). Cell mixture was carefully layered on top of 3 mL of LYMPHOPREP™ density gradient medium (containing 9.1% w/v sodium diatrizoate and 5.7% w/v polysaccharide) (STEMCELL™ Technologies) and centrifuged at 800 RCF for 15 minutes at room temperature. The 9 mL top layer was carefully removed by pipetting and discarded. Ten mL of Wash Buffer was mixed with the remaining 4 mL bottom layer and centrifuged for 10 minutes at 300 RCF at room temperature. The supernatant was decanted, and the cell pellet was resuspended in 10 mL of Wash Buffer. The sample was centrifuged for 10 minutes at 300 RCF at room temperature, supernatant was decanted, and the cell pellet was resuspended in 1.0 mL of DPBS+2% FBS. Cells were counted using a hemocytometer.

CD45 Depletion. The 1.0 mL of cell mixture resulting from density gradient centrifugation was centrifuged at 300 CFS for 10 minutes at room temperature. Cell pellet was reconstituted in 80 µL MACS® Buffer (phosphate buffered saline pH 7.2, 0.5% bovine serum albumin, and 2 mM EDTA) (Miltenyi Biotec), mixed with 20 µL of CD45 MicroBeads (Miltenyi Biotec) and incubated for 15 minutes on ice. The sample was mixed with 1.0 mL of cold MACS® Buffer and centrifuged for 10 minutes at 300 CFS at 4° C. The supernatant was completely removed and discarded. The cell pellet was resuspended in 500 µL of MACS® Buffer. An LS Column (Miltenyi Biotec) was placed in a MIDIMACS® Separator (magnetic cell separator) (Miltenyi Biotec) and washed with 3 mL of MACS® Buffer. Flow-through was discarded. The 500 µL of cell suspension was added to the column. The column was washed 3× with 3 mL of MACS® Buffer. The 9.5 mLs of combined effluent containing the desired CD45-negative cells was centrifuged for 10 minutes at 300 CFS at room temperature. Supernatant was discarded and the cell pellet was resuspended in 1.0 mL of DPBS+2% FBS each. The column containing the magnetically captured CD45-positive cells was discarded.

Array Allocation and Cell Lysis. Ten µL aliquots of the CD45-negative cell mixture were placed into each well of a 96-well microplate. Plates were centrifuged at 800 RCF for 10 minutes at room temperature to pellet cells. The supernatant was removed, and the cell pellets were resuspended in 5 µL of CELLS-TO-SIGNAL™ Lysis Buffer (AMBION®), mixed by pipetting, and incubated at room temperature for 5 minutes. Lysates were frozen at −20° C. until library construction.

Example 2. Library Construction

This example describes preparation of a library for NGS sequencing from cell lysates prepared as described in Example 1.

Reverse Transcription. Whole transcriptome cDNA was synthesized from cell lysates in each well by oligo dT priming in 20 µL reverse transcription reactions. Each reaction contained 20 units of SUPERSCRIPT™ IV Reverse Transcriptase (murine leukemia virus reverse transcriptase with reduced RNase H activity, increased thermostability, and highly efficient full-length cDNA synthesis) (Life Technologies), 1× SUPERSCRIPT™ IV buffer, 5 mM DTT, 0.5 mM dNTP, and 2.5 µM custom-tailed oligo dT primer (SEQ ID NO:2). Lysates, dNTPs, and primer were heated at 65° C. for 5 minutes then cooled on ice. The remaining components were added, and samples were incubated at 50° C. for 10 minutes. The enzyme was inactivated at 80° C. for 10 minutes. The samples were stored at 4° C. until PCR.

Multiplex Target Amplification (PCR #1). Following reverse transcription, 80 µL of PCR 1 pre-mix was added to each 20 µL cDNA reaction. The final concentrations of PCR components after combining with cDNA reactions were 20 mM Tris-HCl (pH 8.5), 25 mM KCl, 4.5 mM $MgCl_2$, 0.2 mM dNTP, 4 units of PLATINUM™ Taq DNA Polymerase (hot-start thermostable DNA polymerase for PCR) (Life Technologies), and 50 nM of each oligo in the Multiplex Primer Pool #RNADNA_v2018_03 (SEQ ID NOS: 2-54). The primer pool, described in more detail below, included 53 oligos targeting 29 mRNA transcripts and 12 genomic DNA sites. Only one transcript-specific primer was used per RNA target (sense-strand), because the oligo dT primer was used to tag the 3' terminus (antisense). Two primers were used per gDNA target site.

Reactions were heated at 95° C. for 5 minutes to denature templates. Amplification was carried out for 20 cycles of 95° C. for 15 s, 65° C. for 90 s, and 72° C. for 30 s. Reactions were held at 68° C. for 5 minutes and then held at 4° C. Each sample was purified by mixing 100 µL sample with 180 µL of AMPURE® XP beads (Beckman Coulter) and incubated at room temperature for 10 minutes. Beads were captured by placing samples in MAGNESPHERE® Separation Stands (magnetic racks) (Promega) and washed 2× with 70% ethanol. Beads were air dried for 10 minutes and resuspended in 30 µL of water. Beads were captured, and supernatant containing purified PCR products were transferred to clean tubes.

Universal PCR and Barcode Integration (PCR #2). Following purification, 25 µL of multiplex PCR products from each well were added to 25 µL of PCR2 pre-mix. The final concentrations of PCR components were 20 mM Tris-HCl (pH 8.5), 50 mM KCl, 1.5 mM $MgCl_2$, 0.2 mM dNTP, 2 units of PLATINUM™ Taq DNA Polymerase (Life Technologies), and 200 nM of each of two universal primers. A first primer that contains sites to facilitate bulk amplification and NGS on ILLUMINA® platforms, P5PM1 (SEQ ID NO:58), was used in every well. The second primer was one of a collection of 96 primers (P7-001 through P7-096 (SEQ ID NOS: 58-153), each containing a unique molecular barcode sequence in addition to the universal sites used for bulk amplification and NGS on ILLUMINA® sequencing platforms. The respective molecular barcodes mark the identity of the well from which each genomic fragment is generated, so only one of these P7 variants was used per well or sample subset.

Reactions were heated at 95° C. for 5 minutes to denature templates. Amplification was carried out for 5 cycles of 95° C. for 15 s, 55° C. for 30 s, and 72° C. for 30 s, followed by 10 cycles of 95° C. for 15 s and 68° C. for 30 s. Reactions were incubated at 68° C. for 5 minutes and then held at 4° C. Each sample was purified using AMPURE® XP beads (Beckman Coulter) as described for PCR #1.

Quantification and Pooling of Subset-Specific Genomic Libraries. Prior to sequencing, the molarity of libraries from each well were quantified by qPCR using the KAPA® Library Quantification Kit for ILLUMINA® Platforms (KAPA BIOSYSTEMS®). Individual libraries were combined at equimolar concentrations to a final pool concentration of 10 nM.

Target-Specific Primer Design: Primers were selected using Primer3 v0.4.0 (see the website bioinfo.ut.ee/primer3-0.4.0/). Custom design settings included primer length (18-27 nt), primer melting temperature (58-63° C.), and product length (140-160 bp). Stringency was lowered for some parameters (e.g., primer length, Tm) with a few targets that failed standard design conditions. A human mispriming library was used to filter all primer designs. Default design parameters were used unless specified.

For gDNA targets, forward and reverse primers were designed to amplify selected target sites, which included cell line mutation sites and TP53 coding exons. Primers were placed in adjacent intronic regions when possible. Input sequences were obtained from Human December 2013 (GRCh38/hg38) Genome Assembly.

For RNA targets, primers were designed to amplify 3' regions of selected mRNA transcripts. Transcript sequences extending up to 300 bp from annotated 3' termini were used as inputs for forward and reverse primer design. Only the forward (sense strand) primer was selected for inclusion in multiplex PCR assays, given that antisense first strand cDNA was carried out with oligo d(T) primers. Input sequences were obtained from NCBI Reference Sequence Database (RefSeq).

Appropriate universal tail sequences were added to the 5' terminus of each TSP (and oligo d(T)) prior to synthesis.

Primer sequences are provided in Table 1. Target names and coordinates are shown in Table 2.

TABLE 1

Primer Sequences

| SEQ ID NO: | SEQUENCE |
|---|---|
| 1 | TGCCCTCACTGTTCT |
| 2 | TGCCCTCACTGTTCTTTTTTTTTTTTTTTTTTVN |
| 3 | TGTGCTCTTCCGATCTCAAGAGAATCCCTCCATCTTTGG |
| 4 | TGTGCTCTTCCGATCTGAGAATGTCACTGTAGTTTTGAGTGT |
| 5 | TGTGCTCTTCCGATCTATTACTGATGTGACTCGGTTTTGTC |
| 6 | TGTGCTCTTCCGATCTTGACAGATAGGCTAGTGGTATTGTG |
| 7 | TGTGCTCTTCCGATCTAAGGTTGTAAAATGTGATGTGTATGTG |
| 8 | TGTGCTCTTCCGATCTTACAACAATTTGTCTGCCTCCAAGG |
| 9 | TGTGCTCTTCCGATCTAAAGCAGTTGAACAAAAATTATGGCATT |
| 10 | TGTGCTCTTCCGATCTTGTTTTAAAATGTTTGGCAGTTCCAC |
| 11 | TGTGCTCTTCCGATCTGGTATTTTCCCCCTTTTCTGCATTT |
| 12 | TGTGCTCTTCCGATCTTGATTGAGCCTCAGAATCATTTGG |
| 13 | TGTGCTCTTCCGATCTCAGTCTACTCAGCTTGACAAGTGTT |
| 14 | TGTGCTCTTCCGATCTGATTGGAGTAGGCTACAGTGAGG |
| 15 | TGTGCTCTTCCGATCTCAGCACGGTGATTAGTCCCAGA |
| 16 | TGTGCTCTTCCGATCTGGATTCATGGGAGCCTCACAG |
| 17 | TGTGCTCTTCCGATCTTTATTTTGAATGATGAGCCTTCGTG |
| 18 | TGTGCTCTTCCGATCTAGACCCTCACTGCTGGGGAGT |
| 19 | TGTGCTCTTCCGATCTTGCATTTATTAACATTTGCAGGACAC |
| 32 | TGCCCTCACTGTTCTCACAGCAGGCCAGTGTGCAG |
| 33 | TGTGCTCTTCCGATCTTTGGGCCTGTGTTATCTCCTAG |
| 34 | TGCCCTCACTGTTCTGAAAAGAGCAGTCAGAGGACCAG |
| 35 | TGTGCTCTTCCGATCTAATTCCATGGGACTGACTTTCTGCT |
| 36 | TGCCCTCACTGTTCTAACCAGCCCTGTCGTCTCTCC |
| 37 | TGTGCTCTTCCGATCTCTTGTGCCCTGACTTTCAACTCTGT |
| 38 | TGCCCTCACTGTTCTCTTAACCCCTCCTCCCAGAGAC |
| 39 | TGTGCTCTTCCGATCTCTCTGATTCCTCACTGATTGCTCT |
| 40 | TGCCCTCACTGTTCTTGGGGAACAAGAAGTGGAGAATG |
| 41 | TGTGCTCTTCCGATCTCAGACCCTCTCACTCATGTGATG |
| 42 | TGCCCTCACTGTTCTCAGGAAGGGGCTGAGGTCACT |
| 43 | TGTGCTCTTCCGATCTACTTCTCCCCCTCCTCTGTTGCT |
| 44 | TGCCCTCACTGTTCTCACTTGATAAGAGGTCCCAAGAC |
| 45 | TGTGCTCTTCCGATCTGTGCAGTTATGCCTCAGATTCAC |
| 46 | TGCCCTCACTGTTCTGTCTCCTCCACCGCTTCTTGTC |
| 47 | TGTGCTCTTCCGATCTTCCTTACTGCCTCTTGCTTCTCTTT |
| 48 | TGCCCTCACTGTTCTTTGCTTTTTCTGTAAATCATCTGTGAA |
| 49 | TGTGCTCTTCCGATCTATGCTGAGATCAGCCAAATTCAGTT |
| 50 | TGCCCTCACTGTTCTTTGGTGATTCCAGTCTGAATGAGTTA |

TABLE 1-continued

Primer Sequences

| SEQ ID NO: | SEQUENCE |
|---|---|
| 51 | TGTGCTCTTCCGATCTAAGCACAGGTCAACACCATCAATTT |
| 52 | TGCCCTCACTGTTCTGTGGACACCAGTTTGGGCTTG |
| 53 | TGTGCTCTTCCGATCTTTTTCCCCCAGAGCATTAGTAGCAT |
| 54 | TGCCCTCACTGTTCTCTGGCAGATCCCAGTCAAGTCAC |
| 55 | TGTGCTCTTCCGATCTAGCAAGTGGTAGGTGACCGTGGAG |
| 20 | TGTGCTCTTCCGATCTGTCTCCAGACAGCTCCATCAGGAA |
| 21 | TGTGCTCTTCCGATCTAGAAGCTGCAAAATCCGATGAGACT |
| 22 | TGTGCTCTTCCGATCTGAAAACCTCCTTTACCAGATGCTGA |
| 23 | TGTGCTCTTCCGATCTAATGGCAACAGGAATTTTCATTGGT |
| 24 | TGTGCTCTTCCGATCTCATGTCTGCACCTCCGCTTG |
| 25 | TGTGCTCTTCCGATCTCATTAAAAGTTGGCCTGAAAGTCAGA |
| 26 | TGTGCTCTTCCGATCTCCAGAACTTGGACTCCATCGTTAAA |
| 27 | TGTGCTCTTCCGATCTATTTTGCAAACAATTTGGAGCCATT |
| 28 | TGTGCTCTTCCGATCTTTCTTAACAACCGACACTCCTACAAGA |
| 29 | TGTGCTCTTCCGATCTAAAGCTTACCAGTGTGGACTTGGTG |
| 30 | TGTGCTCTTCCGATCTACACACATAACAAGTCTATGATCATTTGC |
| 31 | TGTGCTCTTCCGATCTGGCCCACAAGTATCACTAAGCTC |
| 56 | ACACCGCAAGTCCACTAATGCCCTCACTGTTCT |
| 57 | GTGACTGGAGTTCAGACGTGTGCTCTTCCGATCT |
| 58 | AATGATACGGCGACCACCGAGATCAACACCGCAAGTCCACTAATGCCCTCACTGTTCT |
| 59 | CAAGCAGAAGACGGCATACGAGATATCTAGCCGGCCGTGACTGGAGTTCAGACGTGTGCTCTTCCGATC |
| 60 | CAAGCAGAAGACGGCATACGAGATAAGGAAGAGATAGTGACTGGAGTTCAGACGTGTGCTCTTCCGATC |
| 61 | CAAGCAGAAGACGGCATACGAGATGGACGGCATCTAGTGACTGGAGTTCAGACGTGTGCTCTTCCGATC |
| 62 | CAAGCAGAAGACGGCATACGAGATAAGGAAGGAGCGGTGACTGGAGTTCAGACGTGTGCTCTTCCGATC |
| 63 | CAAGCAGAAGACGGCATACGAGATGGACGGCGCTCGGTGACTGGAGTTCAGACGTGTGCTCTTCCGATC |
| 64 | CAAGCAGAAGACGGCATACGAGATCCGGACTCTCGAGTGACTGGAGTTCAGACGTGTGCTCTTCCGATC |
| 65 | CAAGCAGAAGACGGCATACGAGATGGCCGGCCGAGCGTGACTGGAGTTCAGACGTGTGCTCTTCCGATC |
| 66 | CAAGCAGAAGACGGCATACGAGATCCGGACTGAGCTGTGACTGGAGTTCAGACGTGTGCTCTTCCGATC |
| 67 | CAAGCAGAAGACGGCATACGAGATGGACGCGGCAGTGACTGGAGTTCAGACGTGTGCTCTTCCGATC |
| 68 | CAAGCAGAAGACGGCATACGAGATCCGGAGAAGTAAGTGACTGGAGTTCAGACGTGTGCTCTTCCGATC |
| 69 | CAAGCAGAAGACGGCATACGAGATGGCCGCGCGTCAGTGACTGGAGTTCAGACGTGTGCTCTTCCGATC |
| 70 | CAAGCAGAAGACGGCATACGAGATCCGGAGATCATTGTGACTGGAGTTCAGACGTGTGCTCTTCCGATC |
| 71 | CAAGCAGAAGACGGCATACGAGATGGACGTACGCTTGTGACTGGAGTTCAGACGTGTGCTCTTCCGATC |
| 72 | CAAGCAGAAGACGGCATACGAGATAAGGACTGATAAGTGACTGGAGTTCAGACGTGTGCTCTTCCGATC |
| 73 | CAAGCAGAAGACGGCATACGAGATGGACGCGATGACGTGACTGGAGTTCAGACGTGTGCTCTTCCGATC |
| 74 | CAAGCAGAAGACGGCATACGAGATCCGGAGAGACGGGTGACTGGAGTTCAGACGTGTGCTCTTCCGATC |
| 75 | CAAGCAGAAGACGGCATACGAGATGGACGTAGCGAAGTGACTGGAGTTCAGACGTGTGCTCTTCCGATC |
| 76 | CAAGCAGAAGACGGCATACGAGATCCGGAAGAGCGTGTGACTGGAGTTCAGACGTGTGCTCTTCCGATC |

TABLE 1-continued

Primer Sequences

| SEQ ID NO: | SEQUENCE |
|---|---|
| 77 | CAAGCAGAAGACGGCATACGAGATGGCCGCGTACTGGTGACTGGAGTTCAGACGTGTGCTCTTCCGATC |
| 78 | CAAGCAGAAGACGGCATACGAGATAAGGATCAGTACGTGACTGGAGTTCAGACGTGTGCTCTTCCGATC |
| 79 | CAAGCAGAAGACGGCATACGAGATGGCCGTATATCCGTGACTGGAGTTCAGACGTGTGCTCTTCCGATC |
| 80 | CAAGCAGAAGACGGCATACGAGATCCGGAAGCTATGGTGACTGGAGTTCAGACGTGTGCTCTTCCGATC |
| 81 | CAAGCAGAAGACGGCATACGAGATGGCCGATGCCTCGTGACTGGAGTTCAGACGTGTGCTCTTCCGATC |
| 82 | CAAGCAGAAGACGGCATACGAGATCCGGATCCTTATGTGACTGGAGTTCAGACGTGTGCTCTTCCGATC |
| 83 | CAAGCAGAAGACGGCATACGAGATGGACGATCGGAGGTGACTGGAGTTCAGACGTGTGCTCTTCCGATC |
| 84 | CAAGCAGAAGACGGCATACGAGATCCGGATCGAATAGTGACTGGAGTTCAGACGTGTGCTCTTCCGATC |
| 85 | CAAGCAGAAGACGGCATACGAGATGGACGATTAAGAGTGACTGGAGTTCAGACGTGTGCTCTTCCGATC |
| 86 | CAAGCAGAAGACGGCATACGAGATCCGGATCAGGCGGTGACTGGAGTTCAGACGTGTGCTCTTCCGATC |
| 87 | CAAGCAGAAGACGGCATACGAGATGGACGATATTCTGTGACTGGAGTTCAGACGTGTGCTCTTCCGATC |
| 88 | CAAGCAGAAGACGGCATACGAGATCCGGATCTCCGCGTGACTGGAGTTCAGACGTGTGCTCTTCCGATC |
| 89 | CAAGCAGAAGACGGCATACGAGATGGACCGGCCATGGTGACTGGAGTTCAGACGTGTGCTCTTCCGATC |
| 90 | CAAGCAGAAGACGGCATACGAGATAAGGTACGTGACGTGACTGGAGTTCAGACGTGTGCTCTTCCGATC |
| 91 | CAAGCAGAAGACGGCATACGAGATGGACCGGTTGCAGTGACTGGAGTTCAGACGTGTGCTCTTCCGATC |
| 92 | CAAGCAGAAGACGGCATACGAGATCCGGTCAACAGGGTGACTGGAGTTCAGACGTGTGCTCTTCCGATC |
| 93 | CAAGCAGAAGACGGCATACGAGATGGACCTTGGGCTGTGACTGGAGTTCAGACGTGTGCTCTTCCGATC |
| 94 | CAAGCAGAAGACGGCATACGAGATCCGGTACCAAGCGTGACTGGAGTTCAGACGTGTGCTCTTCCGATC |
| 95 | CAAGCAGAAGACGGCATACGAGATGGACCTTCCCGAGTGACTGGAGTTCAGACGTGTGCTCTTCCGATC |
| 96 | CAAGCAGAAGACGGCATACGAGATCCGGTACGTTCGGTGACTGGAGTTCAGACGTGTGCTCTTCCGATC |
| 97 | CAAGCAGAAGACGGCATACGAGATGGCCCTTAAATCGTGACTGGAGTTCAGACGTGTGCTCTTCCGATC |
| 98 | CAAGCAGAAGACGGCATACGAGATAAGGTCAGTTCTGTGACTGGAGTTCAGACGTGTGCTCTTCCGATC |
| 99 | CAAGCAGAAGACGGCATACGAGATGGACCAAGGCGGGTGACTGGAGTTCAGACGTGTGCTCTTCCGATC |
| 100 | CAAGCAGAAGACGGCATACGAGATCCGGTTGCATCAGTGACTGGAGTTCAGACGTGTGCTCTTCCGATC |
| 101 | CAAGCAGAAGACGGCATACGAGATGGCCCAACCGCCGTGACTGGAGTTCAGACGTGTGCTCTTCCGATC |
| 102 | CAAGCAGAAGACGGCATACGAGATCCGGTTGGTAGTGTGACTGGAGTTCAGACGTGTGCTCTTCCGATC |
| 103 | CAAGCAGAAGACGGCATACGAGATGGACCAATTATTGTGACTGGAGTTCAGACGTGTGCTCTTCCGATC |
| 104 | CAAGCAGAAGACGGCATACGAGATCCGGTTGACGACGTGACTGGAGTTCAGACGTGTGCTCTTCCGATC |
| 105 | CAAGCAGAAGACGGCATACGAGATGGCCTGAGATTTGTGACTGGAGTTCAGACGTGTGCTCTTCCGATC |
| 106 | CAAGCAGAAGACGGCATACGAGATCCGGCCGCGCACGTGACTGGAGTTCAGACGTGTGCTCTTCCGATC |
| 107 | CAAGCAGAAGACGGCATACGAGATGGACTGACTAAAGTGACTGGAGTTCAGACGTGTGCTCTTCCGATC |
| 108 | CAAGCAGAAGACGGCATACGAGATCCGGCCGGCGTGGTGACTGGAGTTCAGACGTGTGCTCTTCCGATC |
| 109 | CAAGCAGAAGACGGCATACGAGATGGACTGATCGGGGTGACTGGAGTTCAGACGTGTGCTCTTCCGATC |
| 110 | CAAGCAGAAGACGGCATACGAGATCCGGCCGATACAGTGACTGGAGTTCAGACGTGTGCTCTTCCGATC |
| 111 | CAAGCAGAAGACGGCATACGAGATGGACTCTGAAAGGTGACTGGAGTTCAGACGTGTGCTCTTCCGATC |
| 112 | CAAGCAGAAGACGGCATACGAGATCCGGCGCCGGTAGTGACTGGAGTTCAGACGTGTGCTCTTCCGATC |
| 113 | CAAGCAGAAGACGGCATACGAGATGGACTCTCTTTCGTGACTGGAGTTCAGACGTGTGCTCTTCCGATC |
| 114 | CAAGCAGAAGACGGCATACGAGATAAGGCTAGCCAGGTGACTGGAGTTCAGACGTGTGCTCTTCCGATC |

TABLE 1-continued

Primer Sequences

| SEQ ID NO: | SEQUENCE |
|---|---|
| 115 | CAAGCAGAAGACGGCATACGAGATGGCCTCTTCCCTGTGACTGGAGTTCAGACGTGTGCTCTTCCGATC |
| 116 | CAAGCAGAAGACGGCATACGAGATAAGGCTACGGTCGTGACTGGAGTTCAGACGTGTGCTCTTCCGATC |
| 117 | CAAGCAGAAGACGGCATACGAGATGGACTCTAGGGAGTGACTGGAGTTCAGACGTGTGCTCTTCCGATC |
| 118 | CAAGCAGAAGACGGCATACGAGATAAGGCTATAACTGTGACTGGAGTTCAGACGTGTGCTCTTCCGATC |
| 119 | CAAGCAGAAGACGGCATACGAGATGGACTTCGAGGCGTGACTGGAGTTCAGACGTGTGCTCTTCCGATC |
| 120 | CAAGCAGAAGACGGCATACGAGATAAGGCCGCGACGGTGACTGGAGTTCAGACGTGTGCTCTTCCGATC |
| 121 | CAAGCAGAAGACGGCATACGAGATGGCCTTCCTCCGGTGACTGGAGTTCAGACGTGTGCTCTTCCGATC |
| 122 | CAAGCAGAAGACGGCATACGAGATAAGGCCGGCTGCGTGACTGGAGTTCAGACGTGTGCTCTTCCGATC |
| 123 | CAAGCAGAAGACGGCATACGAGATGGACTTCTCTTAGTGACTGGAGTTCAGACGTGTGCTCTTCCGATC |
| 124 | CAAGCAGAAGACGGCATACGAGATAAGGCCGATCATGTGACTGGAGTTCAGACGTGTGCTCTTCCGATC |
| 125 | CAAGCAGAAGACGGCATACGAGATGGACTTCAGAATGTGACTGGAGTTCAGACGTGTGCTCTTCCGATC |
| 126 | CAAGCAGAAGACGGCATACGAGATAAGGCCGTAGTAGTGACTGGAGTTCAGACGTGTGCTCTTCCGATC |
| 127 | CAAGCAGAAGACGGCATACGAGATGGACTAGGACCAGTGACTGGAGTTCAGACGTGTGCTCTTCCGATC |
| 128 | CAAGCAGAAGACGGCATACGAGATCCGGCTAATGTTGTGACTGGAGTTCAGACGTGTGCTCTTCCGATC |
| 129 | CAAGCAGAAGACGGCATACGAGATGGACTAGCTGGTGTGACTGGAGTTCAGACGTGTGCTCTTCCGATC |
| 130 | CAAGCAGAAGACGGCATACGAGATCCGGCTATACAAGTGACTGGAGTTCAGACGTGTGCTCTTCCGATC |
| 131 | CAAGCAGAAGACGGCATACGAGATGGACTAGTCAACGTGACTGGAGTTCAGACGTGTGCTCTTCCGATC |
| 132 | CAAGCAGAAGACGGCATACGAGATCCGGCTACGTGGGTGACTGGAGTTCAGACGTGTGCTCTTCCGATC |
| 133 | CAAGCAGAAGACGGCATACGAGATGGACTAGAGTTGGTGACTGGAGTTCAGACGTGTGCTCTTCCGATC |
| 134 | CAAGCAGAAGACGGCATACGAGATAAGGCGCGCACAGTGACTGGAGTTCAGACGTGTGCTCTTCCGATC |
| 135 | CAAGCAGAAGACGGCATACGAGATGGCCACAGTACCGTGACTGGAGTTCAGACGTGTGCTCTTCCGATC |
| 136 | CAAGCAGAAGACGGCATACGAGATAAGGGTTAATTTGTGACTGGAGTTCAGACGTGTGCTCTTCCGATC |
| 137 | CAAGCAGAAGACGGCATACGAGATGGCCACATGCAAGTGACTGGAGTTCAGACGTGTGCTCTTCCGATC |
| 138 | CAAGCAGAAGACGGCATACGAGATAAGGGTTCCGGGGTGACTGGAGTTCAGACGTGTGCTCTTCCGATC |
| 139 | CAAGCAGAAGACGGCATACGAGATGGACACAACGTTGTGACTGGAGTTCAGACGTGTGCTCTTCCGATC |
| 140 | CAAGCAGAAGACGGCATACGAGATAAGGGTTGGCCCGTGACTGGAGTTCAGACGTGTGCTCTTCCGATC |
| 141 | CAAGCAGAAGACGGCATACGAGATGGACATGGTGTGGTGACTGGAGTTCAGACGTGTGCTCTTCCGATC |
| 142 | CAAGCAGAAGACGGCATACGAGATCCGGGAACCAAAGTGACTGGAGTTCAGACGTGTGCTCTTCCGATC |
| 143 | CAAGCAGAAGACGGCATACGAGATGGACATGCACACGTGACTGGAGTTCAGACGTGTGCTCTTCCGATC |
| 144 | CAAGCAGAAGACGGCATACGAGATCCGGGAATTGGGGTGACTGGAGTTCAGACGTGTGCTCTTCCGATC |
| 145 | CAAGCAGAAGACGGCATACGAGATGGACATGACACAGTGACTGGAGTTCAGACGTGTGCTCTTCCGATC |
| 146 | CAAGCAGAAGACGGCATACGAGATCCGGGAAGGTTTGTGACTGGAGTTCAGACGTGTGCTCTTCCGATC |
| 147 | CAAGCAGAAGACGGCATACGAGATGGACAACGTCATGTGACTGGAGTTCAGACGTGTGCTCTTCCGATC |
| 148 | CAAGCAGAAGACGGCATACGAGATCCGGGTTAAGGAGTGACTGGAGTTCAGACGTGTGCTCTTCCGATC |
| 149 | CAAGCAGAAGACGGCATACGAGATGGACAACTGACGGTGACTGGAGTTCAGACGTGTGCTCTTCCGATC |
| 150 | CAAGCAGAAGACGGCATACGAGATCCGGGTTCCTTCGTGACTGGAGTTCAGACGTGTGCTCTTCCGATC |
| 151 | CAAGCAGAAGACGGCATACGAGATGGCCAACACTGCGTGACTGGAGTTCAGACGTGTGCTCTTCCGATC |
| 152 | CAAGCAGAAGACGGCATACGAGATCCGGGTTGGAAGGTGACTGGAGTTCAGACGTGTGCTCTTCCGATC |

TABLE 1-continued

Primer Sequences

| SEQ ID NO: | SEQUENCE |
|---|---|
| 153 | CAAGCAGAAGACGGCATACGAGATGGCTGGTCATACGTGACTGGAGTTCAGACGTGTGCTCTTCCGATC |
| 154 | CAAGCAGAAGACGGCATACGAGATCCGAACCTTAGGGTGACTGGAGTTCAGACGTGTGCTCTTCCGATC |
| 155 | GGAGCATTTTGCGGATTATT |
| 156 | TGCATTGGAAGCAAGTGAAC |
| 157 | TAGGGCACCACCACACTATG |
| 158 | GTGGAAGGAAATTTGCGTGT |
| 159 | TCCAGTGGTTTCTTCTTTGG |
| 160 | CTTTCCTAGCACTGCCCAAC |
| 161 | GACAAAGAACAGCTCAAAGCAA |
| 162 | CCTGTGACTCCATAGAAAATCT |
| 163 | TTTGTCCCCCAACTTGAGATGT |
| 164 | CTGGCTGCCTCCACCCACT |
| 165 | TGCCAGACATCACCAGGTTG |
| 166 | GCACTGCTTGGCCCCTACAT |
| 167 | ATACATGTGTGGGTGCTGATAATTGTG |
| 168 | AATTGTTTTCCTTTTCCACCCCCAAA |
| 169 | TGCTTCCACAGTAAAATCTGAAAAA |
| 170 | AGACTCAAGTAAATAGAAAGGCAGCTT |
| 171 | TTGTAAACCTCTTTTGCACTTTGA |
| 172 | GGTTGAGAAAATTGTTTACAGGTGCTC |
| 173 | GGCCCCAATTATCCAATAGTCT |
| 174 | CACCAAAACGAGTTTTTATTACTTCAT |
| 175 | CCATCAAGGTCCAGTGGAAGTTCT |
| 176 | GGGGTCGCTCAGTTTATTGGTAAAA |
| 177 | GTGGTTTTGCTCTCGACAGTATCC |
| 178 | GCAGTGAAGATGAAGGCAACAAAAT |
| 179 | TGTGTATATGGGGGGGACGTGT |
| 180 | ACCCCTAAACAACAGCATAACTCAA |
| 181 | TTCCTTTGTTCCCTAAGTCCAACT |
| 182 | ATGCTCAAGGCCCTTCATAATATC |

TABLE 2

Target Names and Coordinates

| SEQ ID NO: | TARGET NAME | TARGET COORDINATES |
|---|---|---|
| 1 | PM1-TAIL in primer 302 | |
| 2 | PM1-TAIL oligo dT primer | |
| 3 | CD52 mRNA | RefSeq NM_001803.2 (nt 342-504) |
| 4 | CDH1 mRNA | RefSeq NM_004360.4 (nt 4665-4818) |
| 5 | ESR1 mRNA | RefSeq NM_001122742.1 (nt 6308-6463) |

TABLE 2-continued

Target Names and Coordinates

| SEQ ID NO: | TARGET NAME | TARGET COORDINATES |
|---|---|---|
| 6 | HSPB8 mRNA | RefSeq NM_014365.2 (nt 1864-2001) |
| 7 | KITLG mRNA | RefSeq NM_000899.4 (nt 5288-5442) |
| 8 | KRT19 mRNA | RefSeq NM_002276.4 (nt 1313-1470) |
| 9 | MAL2 mRNA | RefSeq NM_052886.2 (nt 2663-2816) |
| 10 | NCOA7 mRNA | RefSeq NM_001199622.1 (nt 3896-4050) |
| 11 | NFKB1 mRNA | RefSeq NM_001165412.1 (nt 3942-4081) |
| 12 | NPY1R mRNA | RefSeq NM_000909.5 (nt 2816-2958) |
| 13 | PGR mRNA | RefSeq NM_000926.4 (nt 12889-13036) |
| 14 | SNTB1 mRNA | RefSeq NM_021021.3 (nt 4835-4974) |
| 15 | TFF1 mRNA | RefSeq NM_003225.2 (nt 341-490) |
| 16 | TPX2 mRNA | RefSeq NM_012112.4 (nt 3507-3662) |
| 17 | ACTB mRNA | RefSeq NM_001101.3 (nt 1648-1811) |
| 18 | GAPDH mRNA | RefSeq NM_001289746.1 (nt 1228-1386) |
| 19 | PTPRC1 mRNA | RefSeq NM_080921.3 (nt 4812-4944) |
| 32 | TP53 EXON 10 gDNA | GRCh38/hg38 chr17:7674141-7674312 |
| 33 | TP53 EXON 10 gDNA | GRCh38/hg38 chr17:7674141-7674312 |
| 34 | TP53 EXON 2 gDNA | GRCh38/hg38 chr17:7676285-7676440 |
| 35 | TP53 EXON 2 gDNA | GRCh38/hg38 chr17:7676285-7676440 |
| 36 | TP53 EXON 4 gDNA | GRCh38/hg38 chr17:7675016-7675280 |
| 37 | TP53 EXON 4 gDNA | GRCh38/hg38 chr17:7675016-7675280 |
| 38 | TP53 EXON 5 gDNA | GRCh38/hg38 chr17:7674819-7674998 |
| 39 | TP53 EXON 5 gDNA | GRCh38/hg38 chr17:7674819-7674998 |
| 40 | TP53 EXON 6 gDNA | GRCh38/hg38 chr17:7669586-7669745 |
| 41 | TP53 EXON 6 gDNA | GRCh38/hg38 chr17:7669586-7669745 |
| 42 | TP53 EXON 7 gDNA | GRCh38/hg38 chr17:7670585-7670742 |
| 43 | TP53 EXON 7 gDNA | GRCh38/hg38 chr17:7670585-7670742 |
| 44 | TP53 EXON 8 gDNA | GRCh38/hg38 chr17:7673505-7673661 |
| 45 | TP53 EXON 8 gDNA | GRCh38/hg38 chr17:7673505-7673661 |
| 46 | TP53 EXON 9 gDNA | GRCh38/hg38 chr17:7673667-7673877 |
| 47 | TP53 EXON 9 gDNA | GRCh38/hg38 chr17:7673667-7673877 |
| 48 | PIK3CA E545K gDNA | GRCh38/hg38 chr3:179218126-179218412 |
| 49 | PIK3CA E545K gDNA | GRCh38/hg38 chr3:179218126-179218412 |
| 50 | EP300_4066 gDNA | GRCh38/hg38 chr22:41168663-41168813 |
| 51 | EP300_4066 gDNA | GRCh38/hg38 chr22:41168663-41168813 |
| 52 | PTPRD_2388 gDNA | GRCh38/hg38 chr9:8492873-8493040 |
| 53 | PTPRD_2388 gDNA | GRCh38/hg38 chr9:8492873-8493040 |
| 54 | PEX14_794 gDNA | GRCh38/hg38 chr1:10629573-10629731 |
| 55 | PEX14_794 gDNA | GRCh38/hg38 chr1:10629573-10629731 |
| 20 | HSPB8 mRNA | RefSeq NM_014365.2 (nt 1819-2001) |
| 21 | HSPB1 mRNA | RefSeq NM_001540.3 (nt 737-896) |
| 22 | NQO1 mRNA | RefSeq NM_000903.2 (nt 2408-2590) |
| 23 | SLC39A6 mRNA | RefSeq NM_001099406.1 (nt 1505-1666) |
| 24 | EEF1A2 mRNA | RefSeq NM_001958.3 (nt 1839-2004) |
| 25 | TMBIM4 mRNA | RefSeq NM_001282606.1 (nt 1830-2003) |
| 26 | EPCAM mRNA | RefSeq NM_002354.2 (nt 1530-1716) |
| 27 | FREM2 mRNA | RefSeq NM_207361.5 (nt 16022-16160) |
| 28 | VIM mRNA | RefSeq NM_003380.3 (nt 1954-2136) |
| 29 | PRC1 mRNA | RefSeq NM_003981.3 (nt 3066-3189) |
| 30 | PTPRC2 mRNA | RefSeq NM_001267798.1 (nt 1305-1466) |
| 31 | HBB mRNA | RefSeq NM_000518.4 (nt 476-626) |
| 56 | PM1-SEQ | |
| 57 | P7-SEQ | |
| 58 | P5PM1 | |
| 59 | P7 INDEX#001 ATCTAGCCGGCC (SEQ ID NO: 182) | |
| 60 | P7 INDEX#002 TATCTCTTCCTT (SEQ ID NO: 183) | |
| 61 | P7 INDEX#003 TAGATGCCGTCC (SEQ ID NO: 184) | |
| 62 | P7 INDEX#004 CGCTCCTTCCTT (SEQ ID NO: 185) | |
| 63 | P7 INDEX#005 CGAGCGCCGTCC (SEQ ID NO: 186) | |
| 64 | P7 INDEX#006 TCGAGAGTCCGG (SEQ ID NO: 187) | |
| 65 | P7 INDEX#007 GCTCGGCCGGCC (SEQ ID NO: 188) | |
| 66 | P7 INDEX#008 AGCTCAGTCCGG (SEQ ID NO: 189) | |
| 67 | P7 INDEX#009 ACTGCCGCGTCC (SEQ ID NO: 190) | |
| 68 | P7 INDEX#010 TTACTTCTCCGG (SEQ ID NO: 191) | |
| 69 | P7 INDEX#011 TGACGCGCGGCC (SEQ ID NO: 192) | |
| 70 | P7 INDEX#012 AATGATCTCCGG (SEQ ID NO: 193) | |
| 71 | P7 INDEX#013 AAGCGTACGTCC (SEQ ID NO: 194) | |
| 72 | P7 INDEX#014 TTATCAGTCCTT (SEQ ID NO: 195) | |
| 73 | P7 INDEX#015 GTCATCGCGTCC (SEQ ID NO: 196) | |
| 74 | P7 INDEX#016 CCGTCTCTCCGG (SEQ ID NO: 197) | |
| 75 | P7 INDEX#017 TTCGCTACGTCC (SEQ ID NO: 198) | |
| 76 | P7 INDEX#018 ACGCTCTTCCGG (SEQ ID NO: 199) | |
| 77 | P7 INDEX#019 CAGTACGCGGCC (SEQ ID NO: 200) | |
| 78 | P7 INDEX#020 GTACTGATCCTT (SEQ ID NO: 201) | |
| 79 | P7 INDEX#021 GGATATACGGCC (SEQ ID NO: 202) | |

TABLE 2-continued

Target Names and Coordinates

| SEQ ID NO: | TARGET NAME | TARGET COORDINATES |
|---|---|---|
| 80 | P7 INDEX#022 CATAGCTTCCGG (SEQ ID NO: 203) | |
| 81 | P7 INDEX#023 GAGGCATCGGCC (SEQ ID NO: 204) | |
| 82 | P7 INDEX#024 ATAAGGATCCGG (SEQ ID NO: 205) | |
| 83 | P7 INDEX#025 CTCCGATCGTCC (SEQ ID NO: 206) | |
| 84 | P7 INDEX#026 TATTCGATCCGG (SEQ ID NO: 207) | |
| 85 | P7 INDEX#027 TCTTAATCGTCC (SEQ ID NO: 208) | |
| 86 | P7 INDEX#028 CGCCTGATCCGG (SEQ ID NO: 209) | |
| 87 | P7 INDEX#029 AGAATATCGTCC (SEQ ID NO: 210) | |
| 88 | P7 INDEX#030 GCGGAGATCCGG (SEQ ID NO: 211) | |
| 89 | P7 INDEX#031 CATGGCCGGTCC (SEQ ID NO: 212) | |
| 90 | P7 INDEX#032 GTCACGTACCTT (SEQ ID NO: 213) | |
| 91 | P7 INDEX#033 TGCAACCGGTCC (SEQ ID NO: 214) | |
| 92 | P7 INDEX#034 CCTGTTGACCGG (SEQ ID NO: 215) | |
| 93 | P7 INDEX#035 AGCCCAAGGTCC (SEQ ID NO: 216) | |
| 94 | P7 INDEX#036 GCTTGGTACCGG (SEQ ID NO: 217) | |
| 95 | P7 INDEX#037 TCGGGAAGGTCC (SEQ ID NO: 218) | |
| 96 | P7 INDEX#038 CGAACGTACCGG (SEQ ID NO: 219) | |
| 97 | P7 INDEX#039 GATTTAAGGGCC (SEQ ID NO: 220) | |
| 98 | P7 INDEX#040 AGAACTGACCTT (SEQ ID NO: 221) | |
| 99 | P7 INDEX#041 CCGCCTTGGTCC (SEQ ID NO: 222) | |
| 100 | P7 INDEX#042 TGATGCAACCGG (SEQ ID NO: 223) | |
| 101 | P7 INDEX#043 GGCGGTTGGGCC (SEQ ID NO: 224) | |
| 102 | P7 INDEX#044 ACTACCAACCGG (SEQ ID NO: 225) | |
| 103 | P7 INDEX#045 AATAATTGGTCC (SEQ ID NO: 226) | |
| 104 | P7 INDEX#046 GTCGTCAACCGG (SEQ ID NO: 227) | |
| 105 | P7 INDEX#047 AAATCTCAGGCC (SEQ ID NO: 228) | |
| 106 | P7 INDEX#048 GTGCGCGGCCGG (SEQ ID NO: 229) | |
| 107 | P7 INDEX#049 TTTAGTCAGTCC (SEQ ID NO: 230) | |
| 108 | P7 INDEX#050 CACGCCGGCCGG (SEQ ID NO: 231) | |
| 109 | P7 INDEX#051 CCCGATCAGTCC (SEQ ID NO: 232) | |
| 110 | P7 INDEX#052 TGTATCGGCCGG (SEQ ID NO: 233) | |
| 111 | P7 INDEX#053 CTTTCAGAGTCC (SEQ ID NO: 234) | |
| 112 | P7 INDEX#054 TACCGGCGCCGG (SEQ ID NO: 235) | |
| 113 | P7 INDEX#055 GAAAGAGAGTCC (SEQ ID NO: 236) | |
| 114 | P7 INDEX#056 CTGGCTAGCCTT (SEQ ID NO: 237) | |
| 115 | P7 INDEX#057 AGGGAAGAGGCC (SEQ ID NO: 238) | |
| 116 | P7 INDEX#058 GACCGTAGCCTT (SEQ ID NO: 239) | |
| 117 | P7 INDEX#059 TCCCTAGAGTCC (SEQ ID NO: 240) | |
| 118 | P7 INDEX#060 AGTTATAGCCTT (SEQ ID NO: 241) | |
| 119 | P7 INDEX#061 GCCTCGAAGTCC (SEQ ID NO: 242) | |
| 120 | P7 INDEX#062 CGTCGCGGCCTT (SEQ ID NO: 243) | |
| 121 | P7 INDEX#063 CGGAGGAAGGCC (SEQ ID NO: 244) | |
| 122 | P7 INDEX#064 GCAGCCGGCCTT (SEQ ID NO: 245) | |
| 123 | P7 INDEX#065 TAAGAGAAGTCC (SEQ ID NO: 246) | |
| 124 | P7 INDEX#066 ATGATCGGCCTT (SEQ ID NO: 247) | |
| 125 | P7 INDEX#067 ATTCTGAAGTCC (SEQ ID NO: 248) | |
| 126 | P7 INDEX#068 TACTACGGCCTT (SEQ ID NO: 249) | |
| 127 | P7 INDEX#069 TGGTCCTAGTCC (SEQ ID NO: 250) | |
| 128 | P7 INDEX#070 AACATTAGCCGG (SEQ ID NO: 251) | |
| 129 | P7 INDEX#071 ACCAGCTAGTCC (SEQ ID NO: 252) | |
| 130 | P7 INDEX#072 TTGTATAGCCGG (SEQ ID NO: 253) | |
| 131 | P7 INDEX#073 GTTGACTAGTCC (SEQ ID NO: 254) | |
| 132 | P7 INDEX#074 CCACGTAGCCGG (SEQ ID NO: 255) | |
| 133 | P7 INDEX#075 CAACTCTAGTCC (SEQ ID NO: 256) | |
| 134 | P7 INDEX#076 TGTGCGCGCCTT (SEQ ID NO: 257) | |
| 135 | P7 INDEX#077 GGTACTGTGGCC (SEQ ID NO: 258) | |
| 136 | P7 INDEX#078 AAATTAACCCTT (SEQ ID NO: 259) | |
| 137 | P7 INDEX#079 TTGCATGTGGCC (SEQ ID NO: 260) | |
| 138 | P7 INDEX#080 CCCGGAACCCTT (SEQ ID NO: 261) | |
| 139 | P7 INDEX#081 AACGTTGTGTCC (SEQ ID NO: 262) | |
| 140 | P7 INDEX#082 GGGCCAACCCTT (SEQ ID NO: 263) | |
| 141 | P7 INDEX#083 CACACCATGTCC (SEQ ID NO: 264) | |
| 142 | P7 INDEX#084 TTTGGTTCCCGG (SEQ ID NO: 265) | |
| 143 | P7 INDEX#085 GTGTGCATGTCC (SEQ ID NO: 266) | |
| 144 | P7 INDEX#086 CCCAATTCCCGG (SEQ ID NO: 267) | |
| 145 | P7 INDEX#087 TGTGTCATGTCC (SEQ ID NO: 268) | |
| 146 | P7 INDEX#088 AAACCTTCCCGG (SEQ ID NO: 269) | |
| 147 | P7 INDEX#089 ATGACGTTGTCC (SEQ ID NO: 270) | |
| 148 | P7 INDEX#090 TCCTTAACCCGG (SEQ ID NO: 271) | |
| 149 | P7 INDEX#091 CGTCAGTTGTCC (SEQ ID NO: 272) | |
| 150 | P7 INDEX#092 GAAGGAACCCGG (SEQ ID NO: 273) | |
| 151 | P7 INDEX#093 GCAGTGTTGGCC (SEQ ID NO: 274) | |
| 152 | P7 INDEX#094 CTTCCAACCCGG (SEQ ID NO: 275) | |
| 153 | P7 INDEX#095 GTATGACCAGCC (SEQ ID NO: 276) | |

TABLE 2-continued

Target Names and Coordinates

| SEQ ID NO: | TARGET NAME | TARGET COORDINATES |
|---|---|---|
| 154 | P7 INDEX#096 CCTAAGGTTCGG (SEQ ID NO: 277) | |
| 155 | chr21_gDNA gDNA | GRCh38/hg38 chr21:14768538-14768637 |
| 156 | chr21_gDNA gDNA | GRCh38/hg38 chr21:14768538-14768637 |
| 157 | DX_TP53_5 gDNA | GRCh38/hg38 chr17:7674872-7674942 |
| 158 | DX_TP53_5 gDNA | GRCh38/hg38 chr17:7674872-7674942 |
| 159 | DX_TP53_8 gDNA | GRCh38/hg38 chr17:7673557-7673617 |
| 160 | DX_TP53_8 gDNA | GRCh38/hg38 chr17:7673557-7673617 |
| 161 | DX_PIK3CA_E545K gDNA | GRCh38/hg38 chr3:179218249-179218335 |
| 162 | DX_PIK3CA_E545K gDNA | GRCh38/hg38 chr3:179218249-179218335 |
| 163 | DX_ACTB mRNA | RefSeq NM_001101.3 (nt 1690-1754) |
| 164 | DX_ACTB mRNA | RefSeq NM_001101.3 (nt 1690-1754) |
| 165 | DX_CD52 mRNA | RefSeq NM_001803.2 (nt 376-468) |
| 166 | DX_CD52 mRNA | RefSeq NM_001803.2 (nt 376-468) |
| 167 | DX_CDH1 mRNA | RefSeq NM_004360.4 (nt 4691-4750) |
| 168 | DX_CDH1 mRNA | RefSeq NM_004360.4 (nt 4691-4750) |
| 169 | DX_EPCAM mRNA | RefSeq NM_002354.2 (nt 1593-1659) |
| 170 | DX_EPCAM mRNA | RefSeq NM_002354.2 (nt 1593-1659) |
| 171 | DX_ESR1 mRNA | RefSeq NM_001122742.1 (nt 6362-6434) |
| 172 | DX_ESR1 mRNA | RefSeq NM_001122742.1 (nt 6362-6434) |
| 173 | DX_PTPRC_1 mRNA | RefSeq NM_080921.3 (nt 4845-4944) |
| 174 | DX_PTPRC_1 mRNA | RefSeq NM_080921.3 (nt 4845-4944) |
| 175 | DX_EEF1A2 mRNA | RefSeq NM_001958.3 (nt 1891-2002) |
| 176 | DX_EEF1A2 mRNA | RefSeq NM_001958.3 (nt 1891-2002) |
| 177 | DX_NQO1 mRNA | RefSeq NM_000903.2 (nt 2442-2527) |
| 178 | DX_NQO1 mRNA | RefSeq NM_000903.2 (nt 2442-2527) |
| 179 | DX_HSPB8 mRNA | RefSeq NM_014365.2 (nt 1885-1944) |
| 180 | DX_HSPB8 mRNA | RefSeq NM_014365.2 (nt 1885-1944) |
| 181 | DX_HBB mRNA | RefSeq NM_000518.4 (nt 529-588) |
| 182 | DX_HBB mRNA | RefSeq NM_000518.4 (nt 529-588) |

Example 3. Detection and Classification of MCF7 Cells in Blood

Overview. Whole blood from healthy donors was collected in Cell-Free DNA BCT blood collection tubes (STRECK®). Five mL of whole blood from one healthy donor was combined with 500,000 MCF7 cells and five mL of whole blood from the same donor was processed without addition of MCF7 cells. Each specimen was mixed with 8 volumes of buffered ammonium chloride solution to selectively lyse erythrocytes. Density gradient centrifugation was then used to separate cells into three fractions. The top and middle layers containing platelets and a significant portion of leukocytes were discarded. The bottom 4 mL fraction containing granulocytes and tumor cells was retained and concentrated by centrifugation. Cell pellets were resuspended in PBS+2% FBS and a dilution series was made in PBS. Diluted fractions were divided into 96-well plates. Cells were lysed and genomic libraries with selected RNA and gDNA targets were generated from each well. Library content was characterized using qPCR analysis. Quantification of an MCF7-specific point mutation in the PIK3CA gene was used to identify wells containing tumor. Quantification of selected RNA transcripts was carried out using diagnostic primers. The process is described in detail below.

Addition of MCF7 Cells. Adherent cells from the MCF7 breast tumor cell line were cultured in 75 mm flasks containing DMEM+10% FBS+1x Antibiotic-Antimycotic (Thermo Fisher Scientific). Cells were dissociated using TRYPLE® Select Enzyme (animal origin-free, recombinant enzyme that cleaves peptide bonds on the C-terminal sides of lysine and arginine, and is a direct replacement for trypsin) (Thermo Fisher Scientific) and counted using a hemocytometer. A total of 500,000 cells in a volume of less than 200 μL was added to one of the two 5 mL blood specimens.

Density Gradient Separation. Five mL of cell resuspension from the RBC lysis procedure (Example 1) were added to 5 mL of room temperature Wash Buffer (PLURISELECT® Life Science) and processed as described in Example 1.

Dilution of Cell Mixture. Cells retained after density gradient separation were diluted in PBS. The ten-fold dilution series for each specimen ranged from 1:10 to 1:100,000.

Array Allocation and Cell Lysis. Cell mixtures were divided and lysed as described in Example 1.

Reverse Transcription. Reverse transcription was carried out as described in Example 2, above.

Multiplex PCR. Multiplex PCR was carried out as described in Example 2, above.

qPCR analysis. The CASTPCR™ TAQMAN® Mutation Assay (castPCR technology to detect and measure somatic mutations in genes) PIK3CA_763_mu (Life Technologies) was used to measure the abundance of a point mutation in MCF7 cells. Several diagnostic SYBR™ Green (fluorescent dye that binds double-stranded DNA molecules by intercalating between the DNA bases) assays were run to quantify RNA targets and the PIK3CA genomic region amplified during library construction (primer sequences provided below).

TAQMAN® (Real-Time PCR Assay) Mutation Assay:
 Hs00000824_mu, PIK3CA_763_mu (Life Technologies Cat #4465804)
SYBR™ Green Exon 12 Assay:

```
Forward primer
                                       (SEQ ID NO: 161)
   5'-GACAAAGAACAGCTCAAAGCAA-3'
```

Reverse primer (SEQ ID NO: 162)

5'-CCTGTGACTCCATAGAAAATCT-3'

Each TAQMAN® reaction contained 2 µL of PCR reaction (diluted 1:100 in water), 5 µL of 2× Fast Advanced Master Mix (Life Technologies), 2.0 µL of water, and 1.0 µL of 10× Mutation Detection Assay Mix Hs00000824_mu, PIK3CA_763_mu (Thermo Fisher Scientific, catalog #4465804). Reactions were run in Fast Mode on a QUANTSTUDIO® 5 Real-Time PCR instrument (Life Technologies).

Each SYBR™ Green reaction contained 2 µL of PCR reaction (diluted 1:100 in water), 5 µL of 2× POWERUP™ SYBR™ Green Master Mix (SYBR™ Green dye, Dual-Lock Taq DNA Polymerase, dNTPs with dUTP/dTTP blend, heat-labile UDG, ROX passive reference dye, and optimized buffer components) (Life Technologies), 2.5 µL of water, and 0.5 µL of 10 µM primer pair. Reactions were run in Fast Mode on a QUANTSTUDIO® 5 Real-Time PCR instrument (Life Technologies).

Data Analysis. All Ct values were converted to abundance using the following formula derived from standard curves:

$$Abundance=10[(Ct-34.231)/-3.558]$$

Normalized PIK3CA mutation frequency (NMF) was calculated using the following formula:

$$NMF=(PIK3CA\_763\_mu\ Abund/PIK3CA\ Exon\ 12\ Abund)\times10{,}000$$

Detection of MCF7-specific mutation. Tumor-containing wells were identified by qPCR detection of PIK3CA c.1633G>A (chr.3 179218303 in GRCh38, COSMIC #763), a heterozygous missense mutation in MCF7 cells.

FIG. 1 shows mutation abundance in a subset of wells from the specimen spiked with MCF7 cells diluted 1:10,000 before arraying into a microplate. Each bar in the graph represents data from one well. The figure shows high mutation signal in Well #4, indicating the presence of one or more MCF7 cells. Two wells from the "blood only" specimen are also shown.

Figure 2:
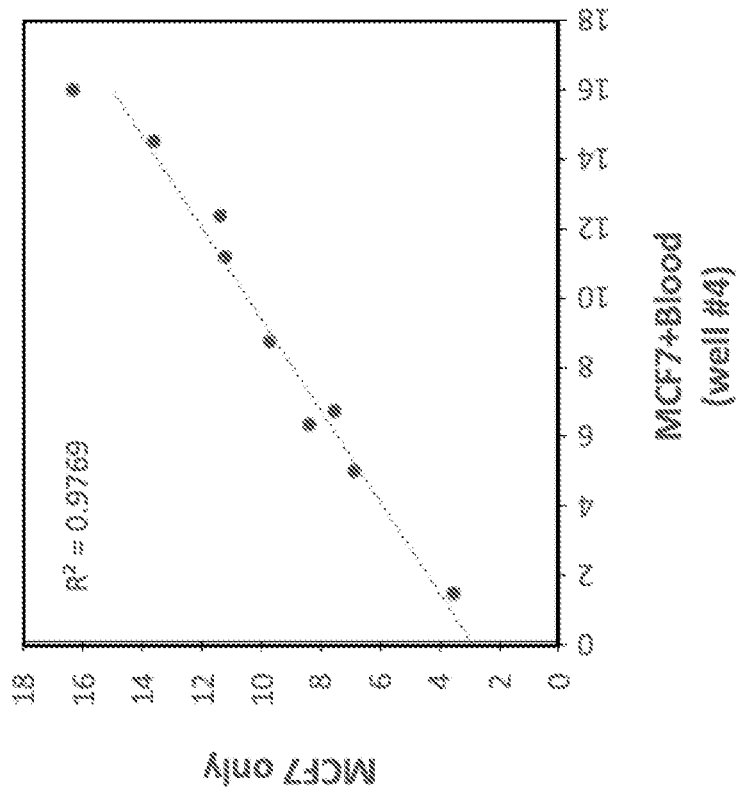
FIG. 2 shows the correlation of RNA abundance in MCF7-positive Well #4 and input MCF7 cells that were not added to blood.

FIG. 2 shows the correlation of RNA abundance in MCF7-positive Well #4 and input MCF7 cells that were not added to blood.

Example 4. Detection of MCF7 Cells in Blood

Overview. Whole blood from healthy donors was collected in Cell-Free DNA BCT blood collection tubes (STRECK®). Five mL of whole blood from one healthy donor was combined with either 100 or 1000 MCF 7 cells. Specimens were mixed with 8 volumes of buffered ammonium chloride solution to selectively lyse erythrocytes. Density gradient centrifugation was then used to separate cells into three fractions. The top and middle layers containing platelets and a significant portion of leukocytes were discarded. The bottom 4 mL fraction containing granulocytes and tumor cells was retained. Each sample was mixed with anti-CD45 beads and bound cells were captured with a magnetic LS column (Miltenyi Biotec). CD45(−) cells, including MCF7, were collected in the column flow-through and concentrated by centrifugation. Cell pellets were resuspended in PBS+2% FBS and the whole volume was divided equally into a 96-well plate without further dilution. Cells were lysed and genomic libraries with selected RNA and gDNA targets were generated from each well. Library content was characterized using qPCR analysis. Quantification of an MCF7-specific point mutation in the PIK3CA gene was used to identify wells containing tumor. The process is described in detail below.

Addition of MCF7 Cells. Adherent cells from the MCF7 breast tumor cell line were cultured in 75 mm flasks containing DMEM+10% FBS+1× Antibiotic-Antimycotic (Thermo Fisher Scientific). Cells were dissociated using TRYPLE® Select Enzyme (Thermo Fisher Scientific) and counted using a hemocytometer. The desired number of cells in a volume of less than 200 µL was added to each 5 mL blood specimen.

Density Gradient Separation. Five mL of a cell resuspension from RBC lysis procedure (Example 1) were added to 5 mL of room temperature Wash Buffer (PLURISELECT® Life Science). An additional blood sample containing 1000 MCF7 cells was processed with density gradient separation alone, serving as a reference to confirm the benefit of adding the CD45 depletion step.

Array Allocation and Cell Lysis. Cell mixtures were divided and lysed as described in Example 1.

Reverse Transcription. Reverse transcription was carried out as described in Example 2, above.

Multiplex PCR. Multiplex PCR was carried out as described in Example 2, above.

qPCR analysis. The CASTPCR™ TAQMAN® Mutation Assay PIK3CA_763_mu (Life Technologies) was used to measure the abundance of a point mutation in MCF7 cells. Several diagnostic SYBR™ Green assays were run to quantify RNA targets and the PIK3CA genomic region amplified during library construction (primer sequences provided below).

TAQMAN® Mutation Assay:
   Hs00000824_mu, PIK3CA_763_mu (Life Technologies Cat #4465804)

SYBRIM Green Exon 12 Assay:

Forward primer (SEQ ID NO: 161)

5'-GACAAAGAACAGCTCAAAGCAA-3'

Reverse primer (SEQ ID NO: 162)

5'-CCTGTGACTCCATAGAAAATCT-3'

Each TAQMAN® reaction contained 2 µL of PCR reaction (diluted 1:100 in water), 5 µL of 2× Fast Advanced Master Mix (Life Technologies), 2.0 µL of water, and 1.0 µL of 10× Mutation Detection Assay Mix Hs00000824_mu, PIK3CA_763_mu (Thermo Fisher Scientific, catalog #4465804). Reactions were run in Fast Mode on a QUANTSTUDIO® 5 Real-Time PCR instrument (Life Technologies).

Each SYBR™ Green reaction contained 2 µL of PCR reaction (diluted 1:100 in water), 5 µL of 2× POWERUP™ SYBR™ Green Master Mix (Life Technologies), 2.5 µL of water, and 0.5 µL of 10 µM primer pair. Reactions were run in Fast Mode on a QUANTSTUDIO® 5 Real-Time PCR instrument (Life Technologies).

Data Analysis. All Ct values were converted to abundance using the following formula derived from standard curves:

$$Abundance=10[(Ct-34.231)/-3.558]$$

Normalized PIK3CA mutation frequency (NMF) was calculated using the following formula:

$$NMF=(PIK3CA\_763\_mu\ Abund/PIK3CA\ Exon\ 12\ Abund)\times10{,}000$$

Detection of MCF7-specific mutation. Tumor-containing wells were identified by qPCR detection of PIK3CA c.1633G>A (chr.3 179218303 in GRCh38, COSMIC #763), a heterozygous missense mutation in MCF7 cells. Data were normalized in all cells to the abundance of PIK3CA exon 12, which spans the region containing the MCF7 mutation. Data collected previously from individual wells of a "blood only" control sample were used to establish a baseline and detection threshold for analysis of MCF7 spiked test samples.

Figure 3:
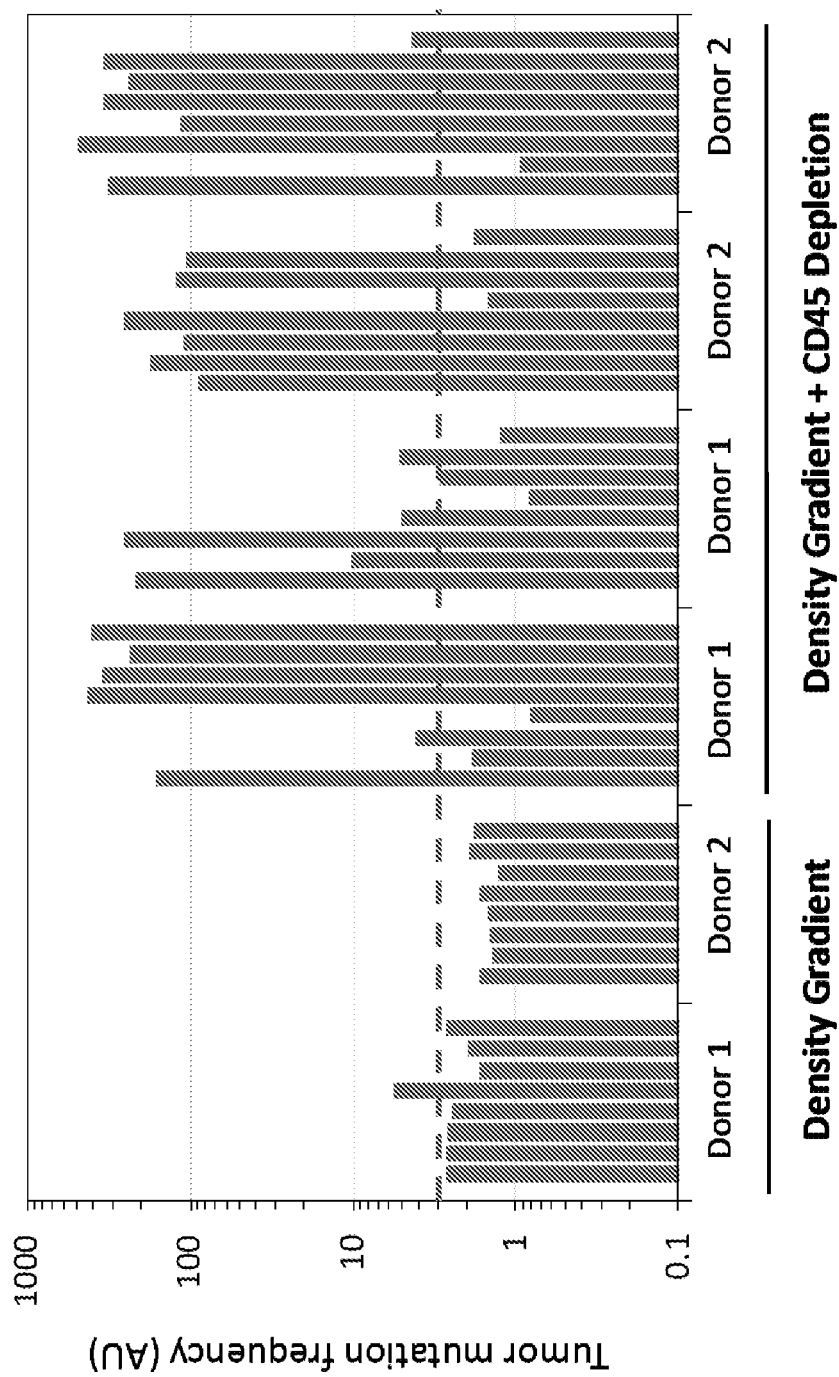
FIG. 3 is a graph showing mutation frequency in individual microwells from specimens processed by density gradient and by density gradient plus CD45 depletion.

FIG. 3 shows mutation frequency in individual microwells from specimens processed by each enrichment method. Each bar in the graph represents data from one well. The dotted line represents the previously described detection threshold. For samples that were processed by density gradient alone, only 1/16 wells yielded mutation signal above background. Even then, the magnitude of the mutation signal in the positive well was near background. In contrast, samples processed by density gradient and CD45 depletion yielded many wells with mutation signal above background. Moreover, the magnitude of the signal in most positive wells was 10-fold or more above background. In donor 1, 11/16 wells were positive as were 13/16 in donor 2 (75% of wells from both donors).

Figure 4:
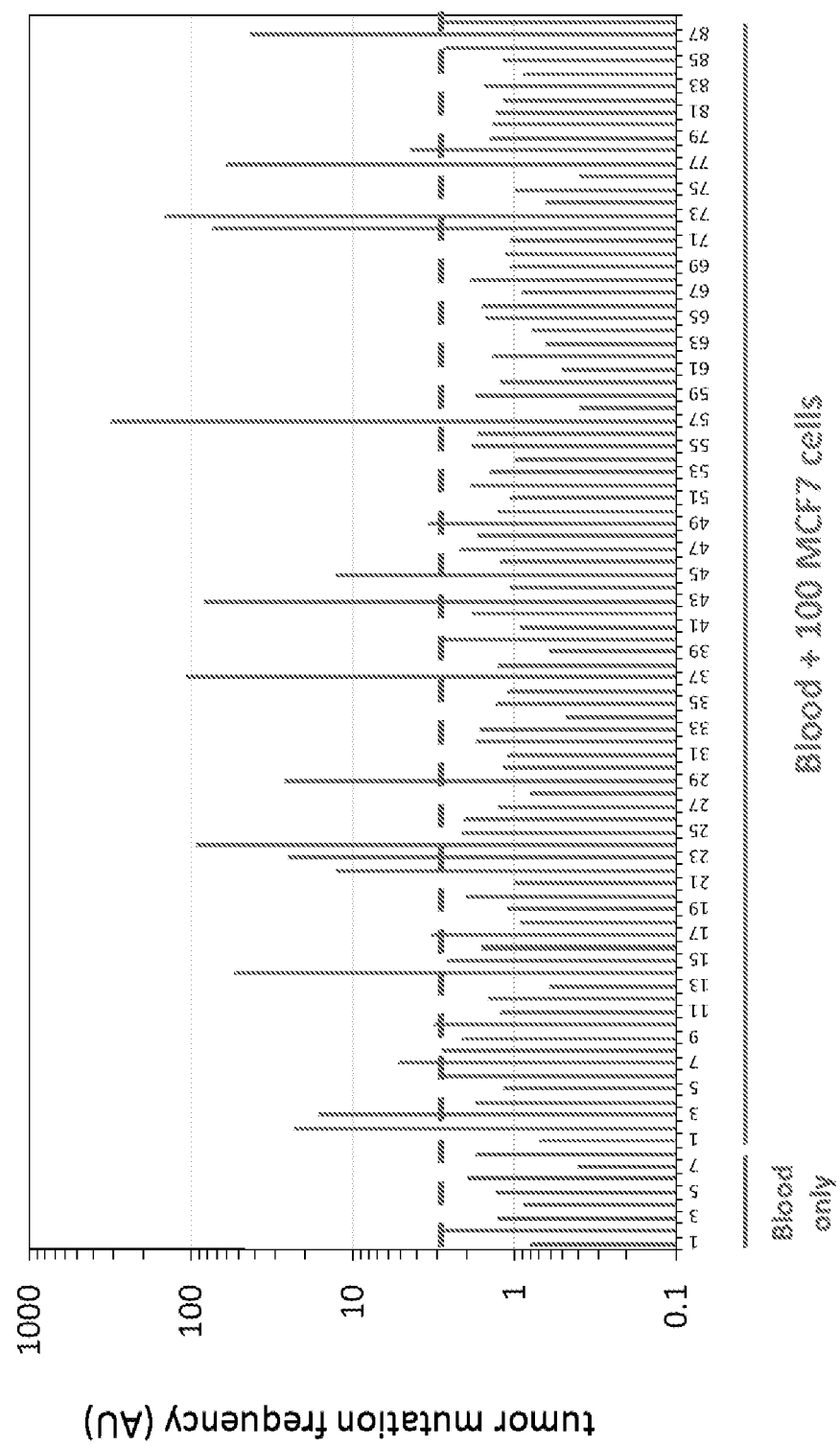
FIG. 4 is a graph showing mutation frequency in individual microwells from blood and from blood spiked with 100 MCF7 cells and processed by density gradient separation plus CD45 depletion.

FIG. 4 shows mutation frequency in individual microwells from specimens processed by density gradient separation plus CD45 depletion. Eight of the 96 wells from the "blood only" sample were tested, whereas 88 of the 96 wells from sample containing 100 MCF7 cells were analyzed. All eight of the "blood only" wells reported mutation signals below the detection threshold (red dotted line) as expected. Of the wells from the MCF7 spike-in sample, 21/88 (24%) reported mutation signal above the detection threshold. A summary of data is shown in Table 3.

TABLE 3

Summary of MCF7 Spike-In Results for Samples Processed by CD45 Depletion

| Sample | No. of Wells Analyzed | No. of Positive Wells- Expected | No. of Positive Wells- Observed | Avg. Mutation Signal in Negative Wells | Avg. Mutation Signal in Positive Wells |
|---|---|---|---|---|---|
| Blood Only | 8 | 0 | 0 | 1.40 | n/a |
| Blood + 100 MCF7 Cells | 88 | 88 | 21 (24%) | 1.38 | 53.0 |
| Blood + 1,000 MCF7 Cells | 32 | 32 | 24 (75%) | 1.50 | 199.0 |

These results demonstrate robust detection of 100 and 1000 tumor cells in 5 mL of whole blood. The magnitude of mutation signal observed in positive wells was high above that of negative wells and tracked with the number of MCF7 cells spiked. In both cases, however, the observed number of positive wells was lower than expected. Both spike-in levels were expected to yield mutation signal in every well tested (1.0 tumor cell per well for 100 cell spike-in and 10 tumor cells per well for 1000 cell spike-in). This difference could be due to a number of factors, such as 1) differential loss of tumor cells during processing, 2) uneven distribution of cells across the array, or 3) sensitivity limits of the qPCR assay used for detection. Using a digital DNA sequencing readout may substantially increase sensitivity of detection.

Example 5. Evaluating CTC Library Content by Next Generation Sequencing

The goal of this experiment was to assess RNA and DNA target content by NGS analysis of libraries constructed from mixtures of purified nucleic acids. In addition, a titration series of MCF7 tumor cell line spiked into healthy donor samples was conducted to obtain an initial assessment of both sensitivity and specificity of tumor detection.

Procedures: NGS libraries were constructed using our previously described RT-PCR protocol (Example 2) and Multiplex Primer Pool #RNADNA_v2018_03 (SEQ ID NOS: 2-54). Purified samples used in this study were obtained from BioChain Institute Inc. (Newark, CA). Sample mixture composition is shown below (units are genomic equivalents).

| Tumor Content: | 0% | 1% | 2% | 4% | 8% | 16% | 32% | 100% |
|---|---|---|---|---|---|---|---|---|
| MCF-7 genomic DNA | 0 | 1 | 2 | 4 | 8 | 16 | 32 | 100 |
| Normal female genomic DNA | 100 | 99 | 98 | 96 | 92 | 84 | 68 | 0 |
| MCF-7 total RNA | 0 | 1 | 2 | 4 | 8 | 16 | 32 | 100 |
| PBMC total RNA (healthy donor) | 100 | 99 | 98 | 96 | 92 | 84 | 68 | 0 |

Barcoded libraries from each microwell were pooled, purified using SPRIselect paramagnetic beads (Beckman Coulter Inc., Indianapolis, IN) and quantified using KAPA® Library Quantification Kits (KAPA BIOSYSTEMS®). NGS was performed on the ILLUMINA® MiSeq System in paired end sequencing format (2×150 bp). Reads were aligned to genome and RNA reference sequences using Bowtie 2. Read counts for each transcript are normalized to the number of reads mapping to human actin beta (ACTB) mRNA (RefSeq NM_001101.3) sequences in each library.

Results. We first assessed the relative proportion of NGS reads that mapped to RNA and gDNA target sites. Libraries constructed from a mixture of RNA and gDNA inputs did produce reads that aligned to both target classes. However, the number of reads mapping to gDNA targets were relatively low (avg. 1.69% of aligned reads, range 1.0-4.4%, n=12) compared to those mapping to RNA targets (avg. 96.1%, range 91.1-97.5%, n=12) even though inputs were 100 cell equivalents for both. Libraries built from gDNA only or RNA only produced reads with high alignment to each of the respective target classes (>99%) as expected. Minor protocol modifications can be made to modulate the ratio of gDNA:RNA target content in sequencing libraries, if desired.

Figure 5A:
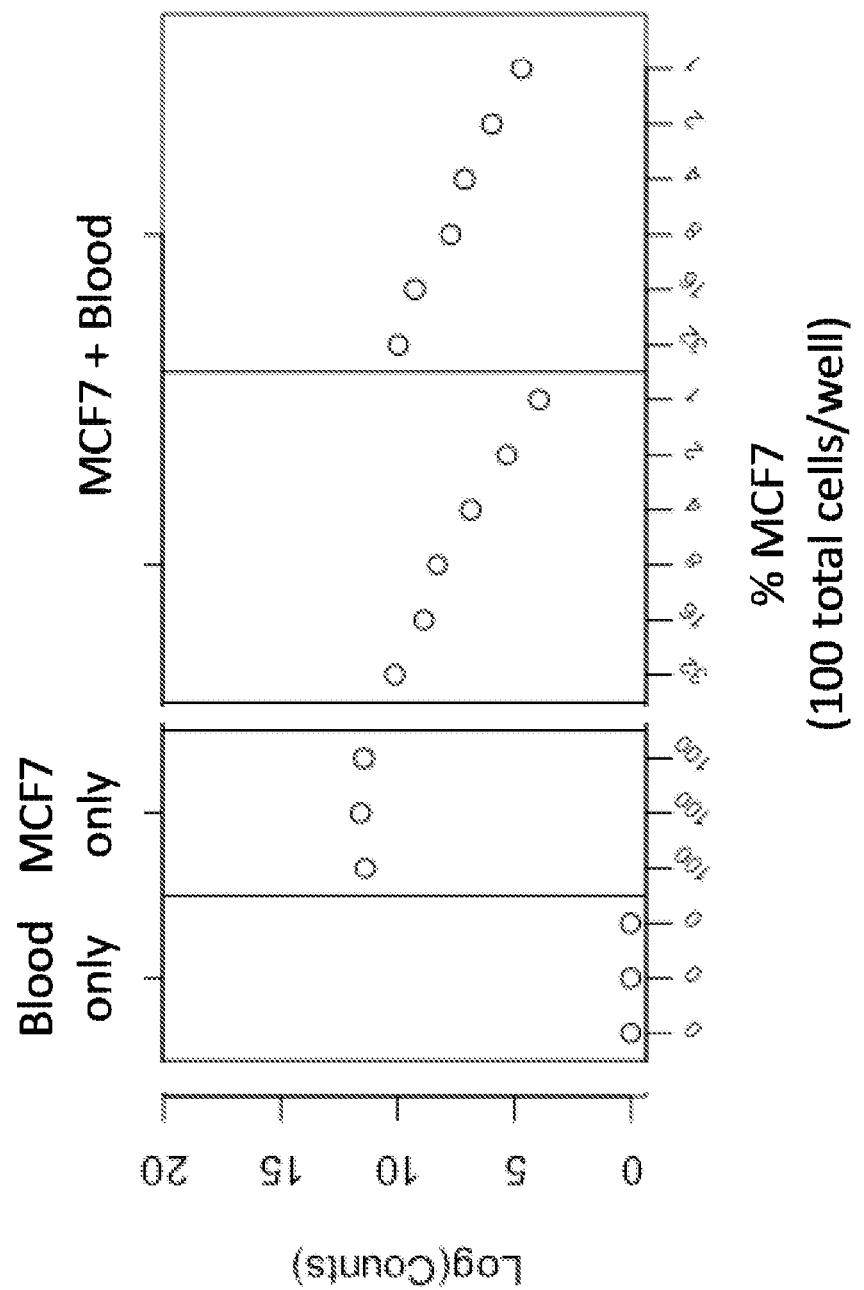
FIG. 5A and FIG. 5B are graphs showing RNA abundance of selected tumor markers (FIG. 5A, EPCAM.
Figure 5B:
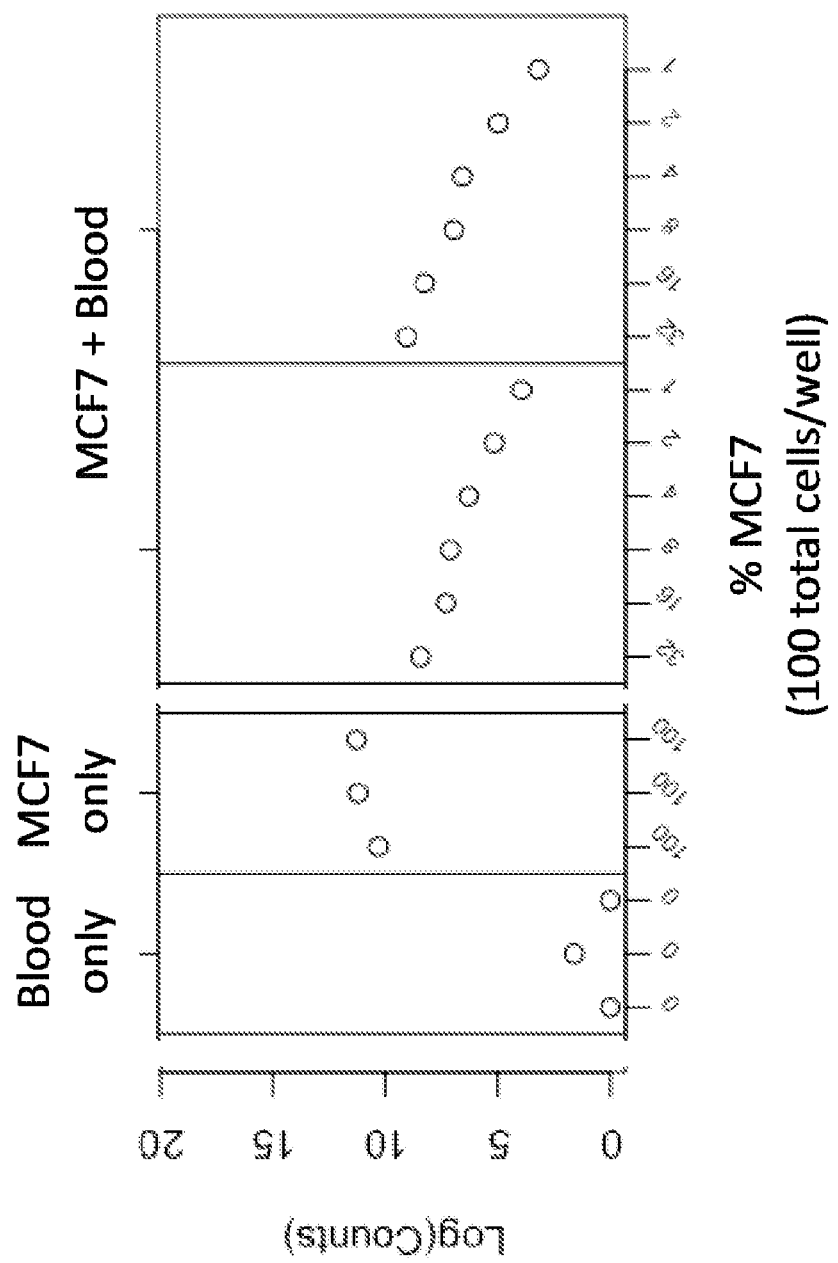
Figure 6B:
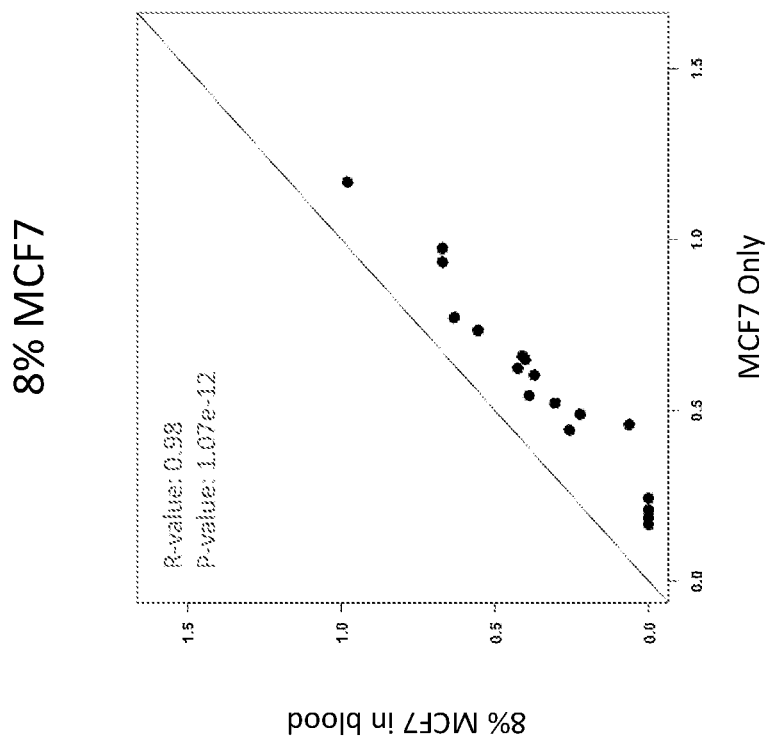
FIGS. 6A-F. Spearman correlation plots of log 2 expression showing detection of MCF7 RNA signature spike-in samples with low tumor content.
Figure 6A:
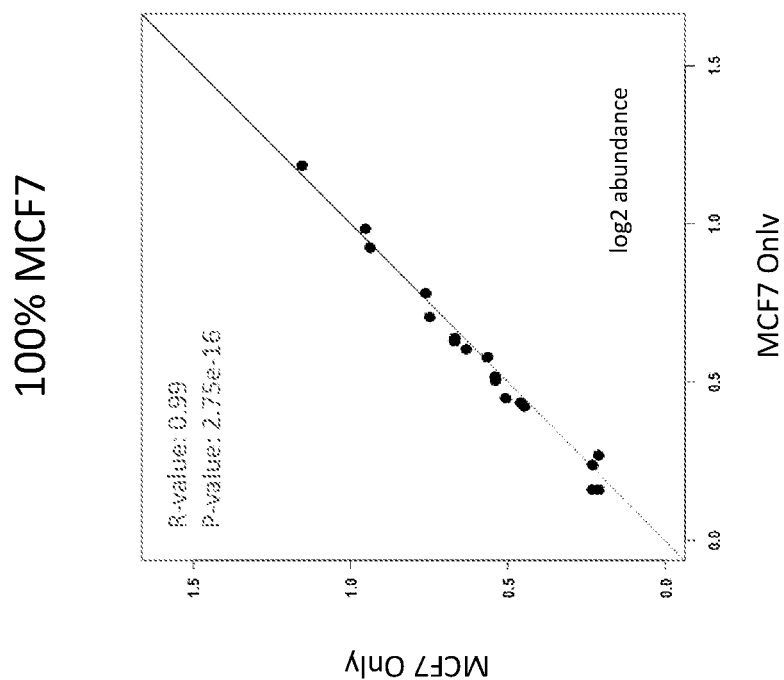
Figure 6D:
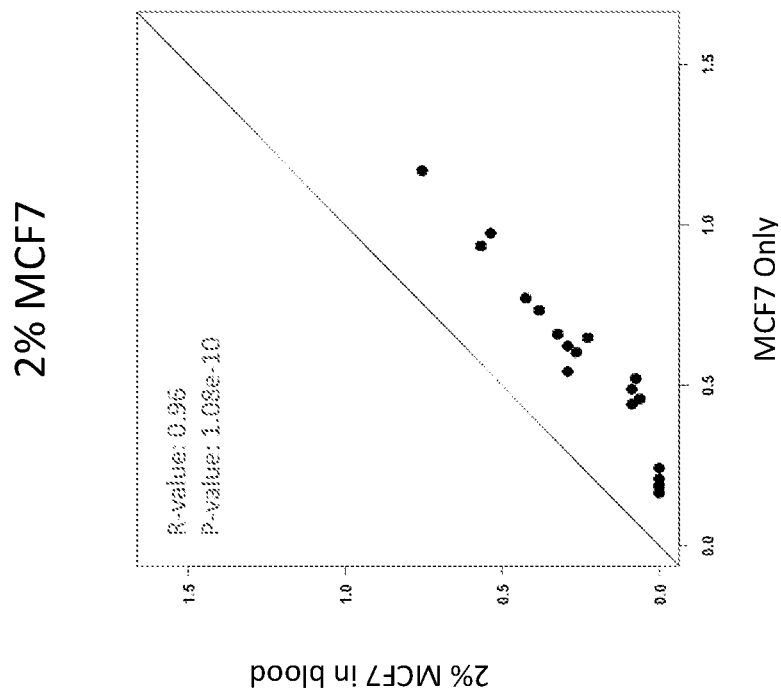
Figure 6C:
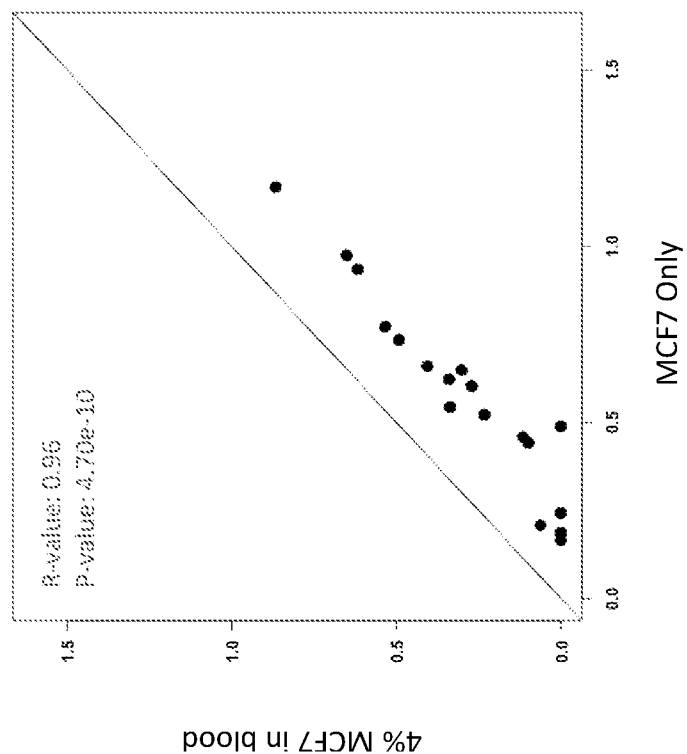
Figure 6E:
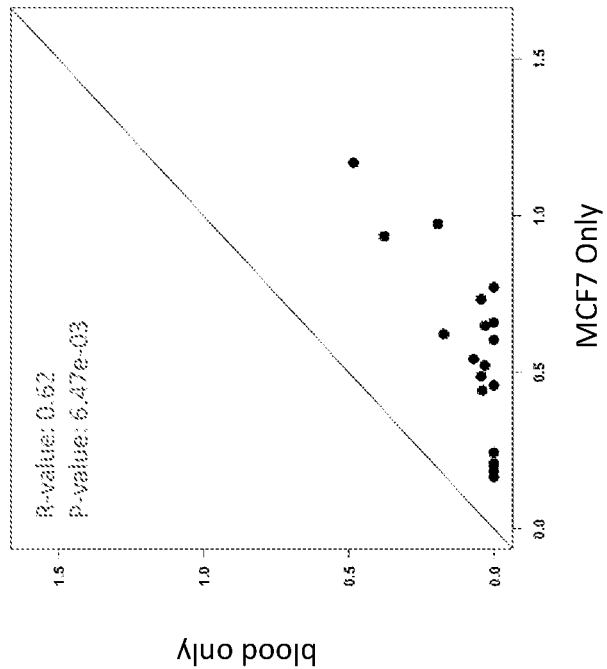
Figure 6F:
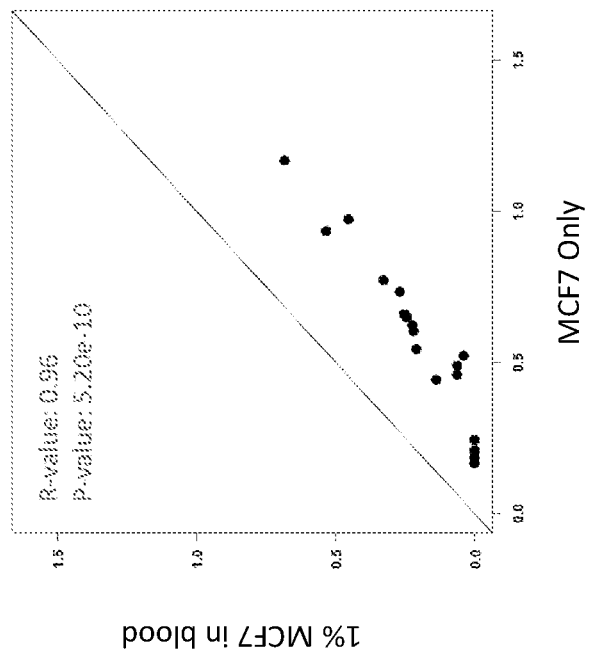

We then evaluated sequences mapping to RNA targets. Transcripts were analyzed at two levels. First, we looked at the expression of individual genes previously reported to be reliable tumor markers (EPCAM, FIG. 5A; and CDH1, FIG. 5B) in CTC assays. Our data confirm that 1) these markers are highly expressed in MCF7 tumor cells, 2) weakly expressed in blood cells, and 3) marker expression varied predictably across tumor titrations. Both tumor markers were robustly detected above blood only background levels even at 1% tumor content (i.e., 1 in 100 cells) and the observed marker expression tracked closely with the expected tumor fraction.

Second, we analyzed tumor RNA signatures over the MCF7 titration series. Twenty tumor markers, selected by comparison of 100% blood and 100% MCF7 libraries, were assessed at tumor spike-in levels ranging from 1% to 8% (FIGS. 6A-F). The MCF7 self-comparison (FIG. 6A) demonstrates an extremely high level of reproducibility over a wide dynamic range. All transcripts shown here exhibited substantially higher expression in MCF7 than blood alone. The tumor signature was readily detected in blood samples containing as little as 1% MCF7 as observed with individual transcripts described in FIGS. 5A and 5B.

The invention claimed is:

1. A method of identifying the presence of a rare cell type in a biological sample, comprising steps of:
   (a) generating, for each of a plurality of nucleic acid subsets of the biological sample, a subset genomic library comprising barcoded double-stranded genomic DNA (gDNA) constructs, wherein the gDNA constructs comprise a first gDNA strand and a second gDNA strand, wherein the first gDNA strand comprises, from 5' to 3':
      (i) a first universal next generation sequencing (NGS) primer comprising, from 5' to 3', a first flow cell adapter sequence; and the nucleotide sequence SEQ ID NO:56;
      (ii) a gDNA sequence of the rare cell type;
      (iii) a sequencing primer for a nucleic acid subset-specific molecular barcode;
      (iv) the nucleic acid subset-specific molecular barcode; and
      (v) a sequence complementary to a second flow cell adapter sequence present on the second gDNA strand;
   (b) pooling the subset genomic libraries to form a combined sequencing library;
   (c) obtaining DNA sequencing reads from the combined sequencing library;
   (d) identifying by means of the nucleic acid subset-specific molecular barcode a nucleic acid subset comprising the gDNA sequence of the rare cell type, thereby identifying the presence of the rare cell type in the biological sample.

2. The method of claim 1, wherein the first universal NGS primer comprises the nucleotide sequence SEQ ID NO:93.

3. The method of claim 1, further comprising quantifying the number of rare cells in the biological sample.

4. The method of claim 1, wherein a nucleic acid alteration specific to the rare cell type comprises a single nucleotide variant, insertion of one or more bases, deletion of one or more bases, addition of a methyl group, removal of a methyl group, increase in DNA copy number or decrease in DNA copy number.

5. The method of claim 1, further comprising, for each of the plurality of nucleic acid subsets of the biological sample:
   (e) reverse transcribing mRNA using a primer comprising the nucleotide sequence SEQ ID NO:2;
   (f) generating a subset expression library comprising barcoded double stranded copy DNA (cDNA) constructs, wherein the cDNA constructs comprise a first cDNA strand and a second cDNA strand, wherein the first cDNA strand comprises, from 5' to 3':
      (i) the first universal NGS primer;
      (ii) a target DNA sequence corresponding to a target mRNA sequence expressed by the rare cell type;
      (iii) the sequencing primer for the nucleic acid subset-specific molecular barcode;
      (iv) the nucleic acid subset-specific molecular barcode; and (v) a sequence complementary to a second flow cell adapter sequence present on the second cDNA strand;

(g) combining the subset expression libraries in the combined sequencing library; and (h) analyzing cDNA constructs comprising the nucleic acid subset-specific molecular barcode of the nucleic acid subset comprising the gDNA of the rare cell type.

6. The method of claim 5, wherein the subset expression library is generated using a primer pool comprising transcript-specific primers.

7. The method of claim 5, wherein the primer pool comprises a primer specific for a biological marker.

8. The method of claim 7, wherein the biological marker is selected from the group consisting of a drug resistance marker, a tissue-specific marker, a drug response marker, and a molecular subtyping marker.

9. The method of claim 1, wherein the biological sample is a blood sample.

10. The method of claim 1, wherein the nucleic acid subsets of the biological sample are generated from subsets of the biological sample comprising 10-1000 cells per subset.

11. The method of claim 1, wherein the rare cell type is selected from the group consisting of a circulating tumor cell (CTC), a circulating epithelial cell (CEC), a stem cell, a progenitor cell, and a rare immune cell.

12. The method of claim 11, wherein the rare cell type is a CTC.

13. The method of claim 11 wherein the rare cell type is a circulating tumor cell cluster comprising two or more tumor cells and one or more cancer stromal cells.

14. An oligo dT primer comprising the nucleotide sequence TGCCCTCACTGTTCTTTTTTTTTTTTTTTTTTTVN (SEQ ID NO:2).

15. A sequencing primer comprising the nucleotide sequence ACACCGCAAGTCCACTAATGCCCTCACTGTTCT (SEQ ID NO:56).

16. A first universal NGS primer comprising, from 5' to 3':
(a) a first flow cell adapter sequence; and
(b) the sequencing primer of claim 15.

17. The first universal NGS primer of claim 16, comprising the nucleotide sequence AATGATACGGCGACCACCGAGATCAACACCGCAAGTCCACTAATGCCCTCACTGTTCT (SEQ ID NO:58).

* * * * *